(12) United States Patent
Smith et al.

(10) Patent No.: US 11,823,371 B2
(45) Date of Patent: Nov. 21, 2023

(54) ASSEMBLY LINE WITH INTEGRATED ELECTRONIC VISUAL INSPECTION

(71) Applicant: Regeneron Pharmaceuticals, Inc., Tarrytown, NY (US)

(72) Inventors: Jason Eugene Smith, Latham, NY (US); Christopher S. Kanel, Hudson, NY (US); Patrick McDonough, Ballston Spa, NY (US); Robert Sterling Nesbitt, East Lyme, CT (US); Taylor MacEwen, Succasunna, NJ (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 159 days.

(21) Appl. No.: 17/214,402

(22) Filed: Mar. 26, 2021

(65) Prior Publication Data
US 2021/0217161 A1    Jul. 15, 2021

Related U.S. Application Data

(63) Continuation of application No. 16/317,039, filed as application No. PCT/US2017/043595 on Jul. 25, 2017, now Pat. No. 10,991,089.
(Continued)

(51) Int. Cl.
*G06T 7/00* (2017.01)
*G06T 7/73* (2017.01)
(Continued)

(52) U.S. Cl.
CPC .......... *G06T 7/0008* (2013.01); *G06Q 50/04* (2013.01); *G06T 7/001* (2013.01); *G06T 7/74* (2017.01);
(Continued)

(58) Field of Classification Search
None
See application file for complete search history.

(56) References Cited

U.S. PATENT DOCUMENTS 7,028,723 B1 *  4/2006  Alouani ................. G16H 20/13
                                                                 141/94
7,070,959 B1    7/2006  Papadopoulos et al.
(Continued)

FOREIGN PATENT DOCUMENTS

CN    102998642 A    3/2013
JP    2012-440 A     1/2012
(Continued)

OTHER PUBLICATIONS

International Search Report, dated Oct. 23, 2017, in International Application No. PCT/US2017/043595 (4 pages).

*Primary Examiner* — Leon Viet Q Nguyen
(74) *Attorney, Agent, or Firm* — Bookoff McAndrews, PLLC

(57) ABSTRACT

Methods and systems are disclosed for obtaining a first image of a tray, determining a presence or absence of one or more first patterns in the first image, determining a rotation of each the one or more first patterns in the first image, and performing an action based on the presence or absence and the rotation of the one or more first patterns in the first image.

21 Claims, 11 Drawing Sheets

Related U.S. Application Data

(60) Provisional application No. 62/368,438, filed on Jul. 29, 2016.

(51) Int. Cl.
  *G06Q 50/04* (2012.01)
  *G16H 20/13* (2018.01)

(52) U.S. Cl.
  CPC ... *G16H 20/13* (2018.01); *G06T 2207/10024* (2013.01); *G06T 2207/30108* (2013.01); *G06T 2207/30164* (2013.01); *G06T 2207/30242* (2013.01)

(56) References Cited

U.S. PATENT DOCUMENTS

| | | | |
|---|---|---|---|
| 7,303,746 B2 | 12/2007 | Wiegand et al. | |
| 7,303,747 B2 | 12/2007 | Wiegand et al. | |
| 7,306,799 B2 | 12/2007 | Wiegand et al. | |
| 7,374,757 B2 | 5/2008 | Papadopoulos et al. | |
| 7,374,758 B2 | 5/2008 | Papadopoulos et al. | |
| 7,531,173 B2 | 5/2009 | Wiegand et al. | |
| 7,608,261 B2 | 10/2009 | Furfine et al. | |
| 7,972,598 B2 | 7/2011 | Daly et al. | |
| 8,029,791 B2 | 10/2011 | Papadopoulos et al. | |
| 8,092,803 B2 | 1/2012 | Furfine et al. | |
| 8,343,737 B2 | 1/2013 | Papadopoulos et al. | |
| 8,647,842 B2 | 2/2014 | Papadopoulos et al. | |
| 9,238,518 B2 | 1/2016 | Luciano, Jr. et al. | |
| 2006/0088196 A1 | 4/2006 | Popovich, Jr. et al. | |
| 2007/0194034 A1 | 8/2007 | Vasiadis | |
| 2009/0317002 A1* | 12/2009 | Dein | A61B 90/90 340/568.1 |
| 2010/0215144 A1* | 8/2010 | Basu | G01V 5/005 378/20 |
| 2013/0135101 A1* | 5/2013 | Kotula | G05B 19/41815 340/540 |
| 2013/0342676 A1* | 12/2013 | Amano | G07F 9/026 348/86 |
| 2015/0170373 A1 | 6/2015 | Yonaha et al. | |
| 2015/0262348 A1* | 9/2015 | Salzman | G06T 7/0004 348/94 |
| 2016/0379361 A1* | 12/2016 | Kim | A61J 7/0076 382/143 |
| 2017/0305589 A1 | 10/2017 | Yuyama et al. | |

FOREIGN PATENT DOCUMENTS

| | | |
|---|---|---|
| JP | 2014-064836 A | 4/2014 |
| JP | 2015-62824 A | 4/2015 |
| JP | 2016-015093 A | 1/2016 |
| KR | 2014-0022805 A | 2/2014 |
| WO | 2011/106900 A1 | 9/2011 |
| WO | 2012-104681 A1 | 8/2012 |
| WO | 2016047569 A1 | 3/2016 |

\* cited by examiner

PASS

PASS

FAIL

PASS

PASS

PASS

PASS

PASS

FAIL

FAIL

ASSEMBLY LINE WITH INTEGRATED ELECTRONIC VISUAL INSPECTION

This application is a continuation of U.S. application Ser. No. 16/317,039, filed Jan. 11, 2019, which is the National Stage Entry of International Application No. PCT/US2017/043595, filed Jul. 25, 2017, which claims priority to U.S. Provisional Application No. 62/368,438, filed on Jul. 29, 2016, each incorporated by reference herein.

BACKGROUND

Assembly of products that contain multiple items, such as pharmaceutical packaging, is a complex task. The assembly can proceed in one or more stages with items being placed into the product at each stage. Errors can be introduced at each stage by failing to place a correct item in the product, placing too many of the correct item in the product, and/or placing an incorrect item in the product. Products that are ultimately shipped with errors result in lost revenue, increased customer complaints, and lost time in addressing the customer complaints. In the case of a pharmaceutical product package, one unintended result of improper packaging is that clinicians or patients may be unwilling to use a pharmaceutical product contained within an improperly assembled package. This can be particularly true for pharmaceutical products that are administered parenterally, e.g., subcutaneously, intramuscularly, intravenously, intra-ocularly, or by inhalation. Even if an improperly assembled package is returned to the manufacturer by a clinician or a patient, a regulatory agency, such as the U.S. Food and Drug Administration, will not allow the pharmaceutical product to be repackaged, resulting in a Notice of Event (NOE). Such NOE's trigger investigations, added expense, and potentially result in an impaired competitive.

It would be desirable, therefore, to develop new technologies for product assembly, that overcomes these and other limitations of the prior art, and enhances it by reducing errors and increasing efficiency of package assembly.

SUMMARY

It is to be understood that both the following general description and the following detailed description are exemplary and explanatory only and are not restrictive. Methods and systems are disclosed for obtaining a first image of a tray, determining a presence or absence of one or more first patterns in the first image, determining a rotation of each the one or more first patterns in the first image, and performing an action based on the presence or absence and the rotation of the one or more first patterns in the first image.

Additional advantages will be set forth in part in the description which follows or may be learned by practice. The advantages will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodiments and together with the description, serve to explain the principles of the methods and systems.

DETAILED DESCRIPTION

Figure 1:
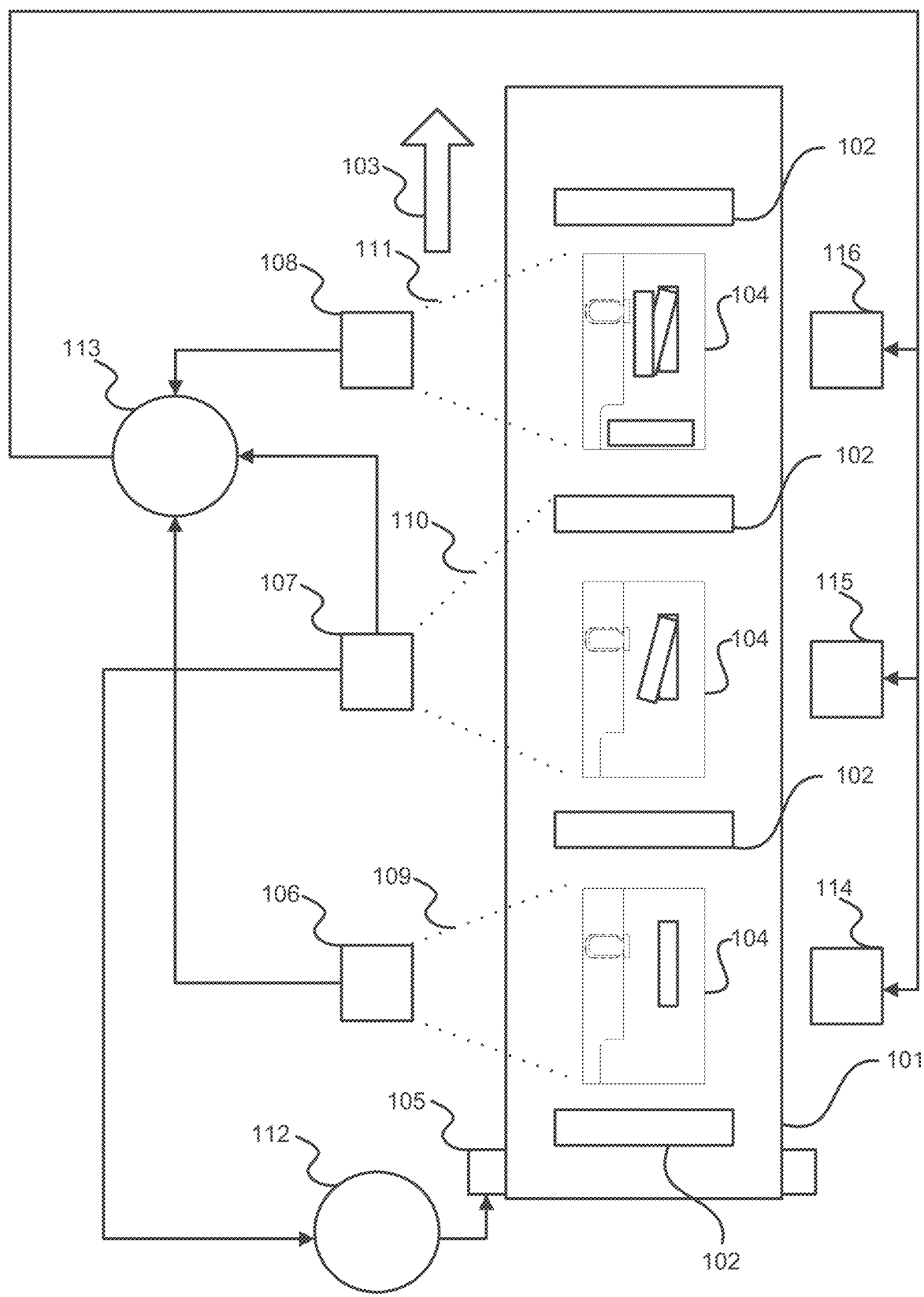
FIG. 1 is an example system.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The present disclosure relates to improvements in computer functionality related to manufacturing and product assembly.

FIG. 1 is a block diagram illustrating various aspects of an exemplary system 100 in which the present methods and systems can operate. One skilled in the art will appreciate that provided herein is a functional description and that the respective functions can be performed by software, hardware, or a combination of software and hardware.

In one aspect, the system 100 can comprise a conveyor belt 101. The conveyor belt 101 can comprise one or more cleats 102. The one or more cleats 102 can be made of rubber or similar material for attachment to the conveyor belt 101. The one or more cleats 102 can be raised or otherwise extend above the surface of the conveyor belt 101. The one or more cleats 102 can comprise a leading cleat and a trailing cleat based on a direction of travel 103. The leading cleat and the trailing cleat can be relative to an object placed on the belt, such that the leading cleat is in front of the object relative to the direction of travel 103 and the trailing cleat is behind the object relative to the direction of travel 103. Accordingly, a leading cleat for a first object can also be a trailing cleat for a second object that is ahead of the first object and so on. One or more objects 104 can be placed on the conveyor belt 101. In an aspect, the one or more objects 104 can comprise a product in one or more states of assembly. For example, the one or more objects 104 can comprise a tray. The tray can be configured to hold one or more items. The one or more items can be related to a medical treatment. For example, the one or more items can comprise one or more syringes, auto injectors, one or more syringe needles, one or more containers of a medicament, one or more pamphlets or sets of written instructions, combinations thereof, and the like.

In one aspect, the set of written instructions sets forth information about how to use and administer a medicament. In another aspect, the written instructions are a medication label approved by a regulatory agency, such as the U.S. Food and Drug Administration.

In one aspect, the medicament is a solid formulation. In another aspect the medicament is a liquid formulation. In another aspect the medicament is a gel formulation.

In one aspect, the medicament is formulated for oral administration. In another aspect the medicament is formulated for parenteral administration. In another aspect the medicament is formulated for subcutaneous administration. In another aspect the medicament is formulated for intramuscular administration. In another aspect the medicament is formulated for intravenous administration. In another aspect the medicament is formulated for inhalation administration. In another aspect the medicament is formulated for intraocular administration.

In one aspect, the medicament comprises a small molecule active ingredient. In another aspect, the medicament comprises a biologic. In another aspect, the medicament comprises a peptide or polypeptide active ingredient.

In one aspect, the medicament comprises a vascular endothelial growth factor (VEGF) derivative active ingredient. In another aspect, the medicament comprises aflibercept, which is described in one or more of U.S. Pat. Nos. 7,070,959; 7,303,746; 7,303,747; 7,306,799; 7,374,757; 7,374,758; 7,531,173; 7,608,261; 7,972,598; 8,029,791; 8,092,803; 8,343,737; 8,647,842, each of which is incorporated by reference in its entirety.

The conveyor belt 101 can pass over a drive roll which can be driven by a stepper motor 105. The use of the stepper motor 105 enables precise positioning of the one or more objects 104 relative to a camera 106, a camera 107, and a camera 108. The length of each of the one or more objects 104 can be represented as a precise number of motor steps. The conveyor belt 101 can be precisely advanced or reversed to cause each of the one or more objects 104 to be moved into a field of view 109, a field of view 110, and a field of view 111, associated with the camera 106, the camera 107, and the camera 108, respectively. A programmable logic controller (PLC) 112 (the PLC 112 can comprise a computing device, a PLC, or other controller/processor) can be configured to cause the stepper motor 105 to execute any number of steps in either direction to cause the one or more objects 104 to be moved into the field of view 109, the field of view 110, and the field of view 111.

In an aspect, the camera 106, the camera 107, and/or the camera 108 can be configured for scanning, decoding, reading, sensing, imaging, capturing, and/or interpreting visual codes. In some aspects, the camera 106, the camera 107, and/or the camera 108 can be configured to process laser, linear, or area imaging. For example, in one aspect, the camera 106, the camera 107, and/or the camera 108 may include an imager for scanning, reading, and decoding one-dimensional or two-dimensional barcodes. The camera 106, the camera 107, and/or the camera 108 can include any imager, barcode scanner, or visual code scanner capable of extracting information from visual codes consistent with the disclosed embodiments. In certain aspects, the camera 106, the camera 107, and/or the camera 108 can be configured to process scanned barcodes, images, and other data. The camera 106, the camera 107, and/or the camera 108 can include one or more depth cameras for capturing, processing, sensing, observing, modeling, detecting, and interacting with three-dimensional environments. In certain aspects, the camera 106, the camera 107, and/or the camera 108 can recognize and detect depths and colors of objects in the field of view 109, the field of view 110, and the field of view 111, respectively. The camera 106, the camera 107, and/or the camera 108 can also provide other camera and video recorder functionalities, such as taking pictures, recording videos, streaming images or other data, storing data in image buffers, etc. These functionalities may or may not include depth information. In connection with hardware and/or software processes consistent with the disclosed embodiments, the camera 106, the camera 107, and/or the camera 108 can determine sizes, orientations, and visual properties of the one or more objects 104. The camera 106, the camera 107, and/or the camera 108 can include or embody any camera known to one of ordinary skill in the art capable of handling the processes disclosed herein. The camera 106, the camera 107, and/or the camera 108 can include appropriate hardware and software components (e.g., circuitry, software instructions, etc.) for transmitting signals and information to and from a pass/fail controller 113 to conduct processes consistent with the disclosed embodiments. The pass/fail controller can 113 comprise a computing device, a PLC, or other controller/processor. The camera 106, the camera 107, and/or the camera 108 can output an image and/or one or more notifications to a monitor 114, a monitor 115, and a monitor 116, respectively.

Positioning of the one or more objects 104 into the field of view 109, the field of view 110, and the field of view 111 can occur at a start-up of the system 100 and can be adjusted during use of the system 100. One or more of the camera 106, the camera 107, and/or the camera 108 can be used to ensure proper positioning of the conveyor belt 101. For example, the camera 107 can be configured to generate an image of the area within the field of view 110. The camera 107 can determine a location of the one or more cleats 102 in the image. In an aspect, the camera 107 can determine the location of the leading cleat. The camera 107 can compare the determined location of the one or more cleats 102 in the image to a reference location. If the determined location is equal to the reference location then no adjustment is necessary to the conveyor belt 101. If the determined location is not equal to the reference location, the camera 107 can determine an offset based on the difference between the determined location and the reference location. The offset can be determined in a measure of distance, for example, millimeters, centimeters, inches, and the like and/or the offset can be determined as a number of steps. The camera 107 can transmit a signal to the PLC 112 to advance or reverse the conveyor belt 101 by the offset by engaging the stepper motor 105.

In operation, the system 100 can be configured to assess a current state of assembly of the one or more objects 104 and take one or more actions based on the current state of assembly. As each of the one or more objects 104 is advanced by the conveyor belt 101, the one or more objects 104 will each be placed in the field of view 109, the field of view 110, and the field of view 111 of the camera 106, the camera 107, and/or the camera 108, respectively. While FIG. 1 illustrates only three cameras, it is specifically contemplated that less than three or more than three cameras can be used. It is further contemplated that the conveyor belt 101 can be configured to have more than the illustrated three objects 104 disposed thereon, regardless of the number of cameras. As the one or more objects 104 progress along the conveyor belt 101, one or more items can be assembled into the one or more objects 104 by a human operator or a robot.

When each of the one or more objects 104 is within a field of view of one of the cameras, the camera can generate an image of the object 104 within the field of view associated with that camera. For example, the camera 106 can generate an image of the area within the field of view 109, the camera 107 can generate an image of the area within the field of view 110, and the camera 108 can generate an image of the area within the field of view 111. Each of the camera 106, the camera 107, and/or the camera 108 can analyze their respective images. The analysis of an image can comprise determining a presence or absence of one or more patterns. The one or more patterns can comprise a text pattern, a numeric pattern, a symbol pattern, and combinations thereof. For example, a text pattern can comprise any sequence of characters such as, "FILTER NEEDLE". A numeric pattern can comprise any sequence of numbers such as, "6941518". The symbol pattern can comprise any sequence of symbols such as, "●□□■". In an aspect, the camera 106, the camera 107, and/or the camera 108 can utilize optical character recognition (OCR) to "read" the one or more patterns. In another aspect, the camera 106, the camera 107, and/or the camera 108 can be configured to not utilize OCR, but rather can be configured to merely recognize the one or more patterns as a specific pattern.

In an aspect, the one or more patterns can be embodied on the one or more items to be assembled into the one or more objects 104. In an aspect, at least a portion of the one or more items can comprise one or more associated patterns. Thus, in the event the camera 106, the camera 107, and/or the camera 108 determines the presence of the one or more patterns, the presence of the one or more patterns indicates a presence of the item associated with a specific pattern. For example, if the camera 106 determines the presence of "FILTER NEEDLE" in the image taken of the area within the field of view 109, then a conclusion can be drawn that an item associated with the pattern "FILTER NEEDLE" is present in the object 104 within the field of view 109. The camera 106, the camera 107, and/or the camera 108 can be configured to determine the presence or absence of a plurality of patterns within a single image. For example, the camera 106 can determine the presence of "FILTER NEEDLE" and "FILTER NEEDLE" in the image taken of the area within the field of view 109. The presence of both patterns can indicate that an item associated with two occurrences of the pattern "FILTER NEEDLE" is present in the object 104 within the field of view 109.

Each of the items that can be assembled into the one or more objects 104 can be associated with one or more patterns that indicate a presence or absence of a specific number of the item. For example, an item may only be embodied with one occurrence of a specific pattern. If the camera 106, the camera 107, and/or the camera 108 determine that the specific pattern only occurs once then the conclusion can be drawn that only one of the item is present. However, if the camera 106, the camera 107, and/or the camera 108 determine that the specific pattern occurs two or more times then the conclusion can be drawn that more than one of the item is present. In another example, an item may be embodied with two occurrences of a specific pattern. If the camera 106, the camera 107, and/or the camera 108 determine that the specific pattern only occurs twice then the conclusion can be drawn that only one of the item is present. However, if the camera 106, the camera 107, and/or the camera 108 determine that the specific pattern occurs one or three or more times then the conclusion can be drawn that more than one of the item is present. In a further example, an item may be embodied with a range of specific patterns. For example, the item may be embodied with one to two occurrences of the specific pattern. If the camera 106, the camera 107, and/or the camera 108 determine that the specific pattern occurs once or twice then the conclusion can be drawn that only one of the item is present. However, if the camera 106, the camera 107, and/or the camera 108 determine that the specific pattern occurs three or more times then the conclusion can be drawn that more than one of the item is present.

Figure 2:
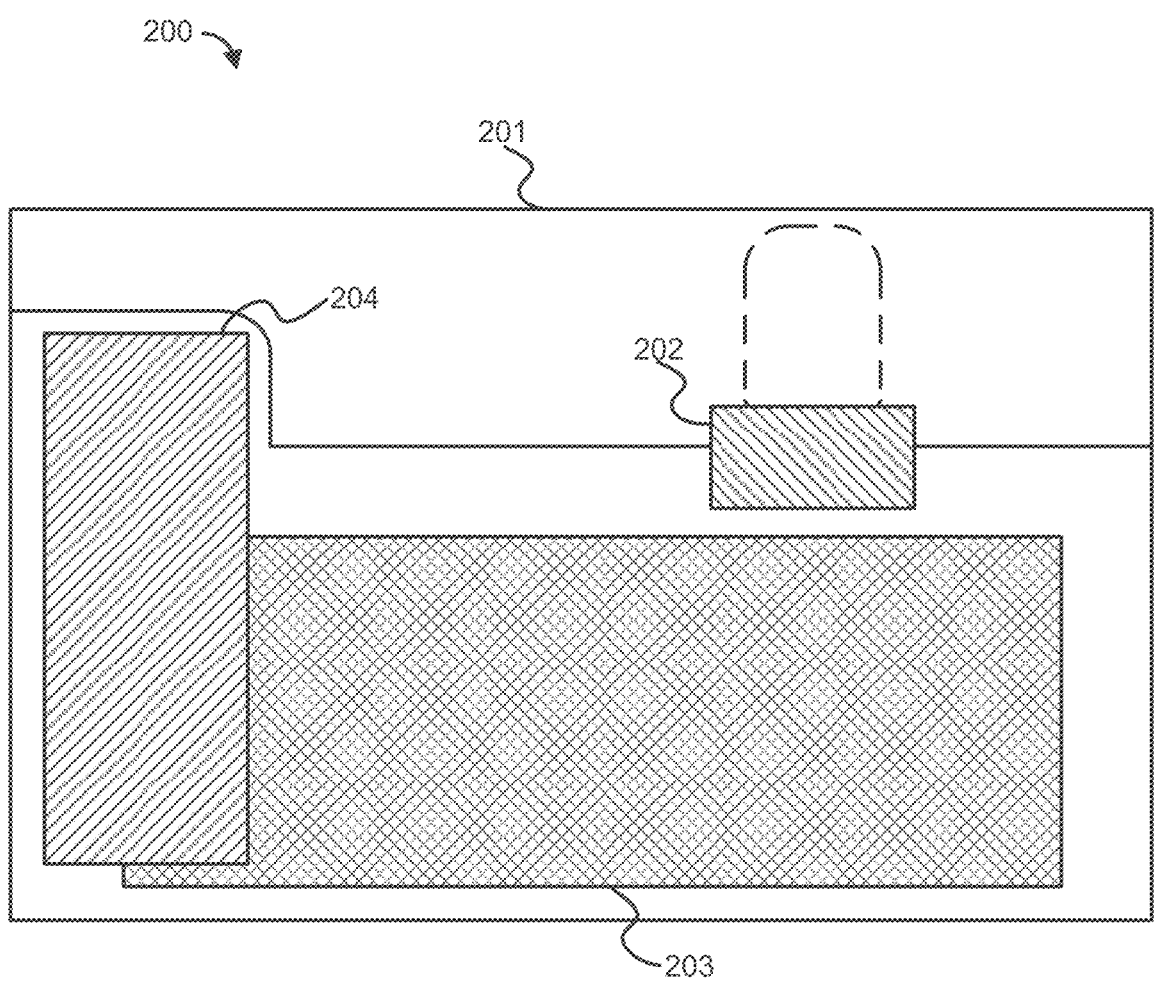
FIG. 2 is an example image of an object.

Each of the camera 106, the camera 107, and/or the camera 108 can be configured to analyze an entire image or one or more specific regions of an image. FIG. 2 illustrates an example image 200 of an object 104. The object 104 can comprise a tray 201 configured for storing one or more items. The one or more items can be assembled into the tray 201 such that at least a portion of the one or more items is present in one or more specific regions. The tray 201 can comprise one or more regions, for example, a region 202, a region 203, and a region 204. Each of the region 202, the region 203, and the region 204 can be associated with an area where the one or more patterns should be present if the item is present in the tray 201. For example, the region 202 can be associated with a location of a vial cap of a vial when assembled into the tray 201, the region 203 can be associated with a location of one or more syringes and/or one or more needles when assembled into the tray 201, and the region 204 can be associated with a location of one or more pamphlets when assembled into the tray 201. Each of the camera 106, the camera 107, and/or the camera 108 can be configured to analyze one or more assigned regions of the image 200. For example, the camera 106 can be assigned to analyze the region 202 and the region 203, the camera 107 can be assigned to analyze the region 203, and the camera 108 can be assigned to analyze the region 203 and the region 204. Any combination of assigned regions is contemplated. Furthermore, each of the camera 106, the camera 107, and/or the camera 108 can be configured to determine presence or absence of one or more assigned patterns in the assigned regions. For example, the camera 106 can be assigned to determine presence or absence of a vial cap in the region 202 and presence or absence of a first pattern (including a number of occurrences of the first pattern) in the region 203, the camera 107 can be assigned to determine presence or absence of a second pattern (including a number of occurrences of the second pattern) in the region 203, and the camera 108 can be assigned to determine presence or absence of a third pattern (including a number of occurrences of the third pattern) in the region 203 and presence or absence of a fourth pattern (including a number of occurrences of the fourth pattern) in the region 204. Any combination of assigned patterns and assigned regions is contemplated.

Returning to FIG. 1, each of the one or more objects 104 can be configured to contain a specific number of each of the one or more items. The presence of the specific number of each item indicates that the one or more objects 104 is correctly assembled. The presence of anything other than the specific number of each item indicates that the one more objects 104 is incorrectly assembled. Each of the camera 106, the camera 107, and/or the camera 108 can be configured to make an independent assessment of the object 104 within the respective field of view. If a camera determines that the specific number of items the camera is configured to detect is present, the camera can issue a PASS signal to the pass/fail controller 113. If a camera determines that the specific number of items the camera is configured to detect is not present, the camera can issue a FAIL signal to the pass/fail controller 113. If each of the camera 106, the camera 107, and/or the camera 108 issues a PASS signal to the pass/fail controller 113, then the pass/fail controller 113 can provide a signal to the PLC 112 to cause the stepper motor 105 to advance the conveyor belt 101 to advance the one or more objects 104 to be positioned under the field of view of the next camera. The pass/fail controller 113 can further transmit a notification to each of the monitors 114-116 to display a PASS notification. If one or more of the camera 106, the camera 107, and/or the camera 108 issues a FAIL signal to the pass/fail controller 113, the pass/fail controller 113 will not provide a signal to the PLC 112 to cause the stepper motor 105 to advance. The pass/fail controller 113 can further transmit a notification to the monitors 114-116 associated with the camera(s) issuing the FAIL signal to display a FAIL notification. An operator (e.g., a human or a robot) positioned at the monitors 114-116 displaying the FAIL notification can take corrective action to remedy the FAIL status. For example, if the FAIL signal was issued as a result of a missing item, the operator can replace the missing item whereupon the camera that made the prior FAIL determination can re-generate and re-analyze an image to determine that the item is now present and issue a PASS signal to the pass/fail controller 113. In another example, if the FAIL signal was issued as a result of one or more extra items, the operator can remove the one or more extra items whereupon the camera that made the prior FAIL determination can re-generate and re-analyze an image to determine that the required number of items is now present and issue a PASS signal to the pass/fail controller 113.

In a further aspect, the analysis of an image by the camera 106, the camera 107, and/or the camera 108 can comprise not only determining the presence of absence of the one or more patterns, but also determining a rotation of two or more patterns. In an aspect, the two or more patterns can be embodied on the one or more items to be assembled into the one or more objects 104 along a specific axis. In an aspect, at least a portion of the one or more items can comprise two or more associated patterns along a specific axis. Thus, in the event the camera 106, the camera 107, and/or the camera 108 determines the presence of the two or more patterns along the specific axis, the presence of the two or more patterns along the specific axis indicates a presence of the item associated with a specific pattern along the specific axis. For example, if the camera 106 determines the presence of "FILTER NEEDLE" and "FILTER NEEDLE" along the same axis (e.g., 30°, 60°, 90°, 120°, 180°, and the like) in the image taken of the area within the field of view 109, then a conclusion can be drawn that an item associated with the pattern "FILTER NEEDLE" and "FILTER NEEDLE" along the same axis is present in the object 104 within the field of view 109. The camera 106, the camera 107, and/or the camera 108 can be configured to determine the rotation of a plurality of patterns within a single image. For example, the camera 106 can determine the presence of "FILTER NEEDLE" and "FILTER NEEDLE" along a first axis and the presence of "SYRINGE NEEDLE" and "SYRINGE NEEDLE" along a second axis in the image taken of the area within the field of view 109. The presence of both patterns along two different axes can indicate that an item associated with two occurrences of the pattern "FILTER NEEDLE" along the first axis is present in the object 104 and an item associated with two occurrences of the pattern "SYRINGE NEEDLE" along the second axis is also present in the object 104. By way of further example, the camera 106 can determine the presence of "FILTER NEEDLE" and "FILTER NEEDLE" along a first axis and the presence of "FILTER NEEDLE" along a second axis in the image taken of the area within the field of view 109. The presence of both patterns along two different axes can indicate that two occurrences of an item associated with the pattern "FILTER NEEDLE" are present in the object 104.

Each of the items that can be assembled into the one or more objects 104 can be associated with one or more patterns that are embodied along a specific axis that indicate a presence or absence of a specific number of the item. For example, an item may be embodied with two occurrences of a specific pattern along a specific axis. If the camera 106, the camera 107, and/or the camera 108 determine that the specific pattern only occurs twice along the specific axis then the conclusion can be drawn that only one of the item is present. However, if the camera 106, the camera 107, and/or the camera 108 determine that the specific pattern occurs along more than one axis then the conclusion can be drawn that more than one of the item is present.

Figure 3A:
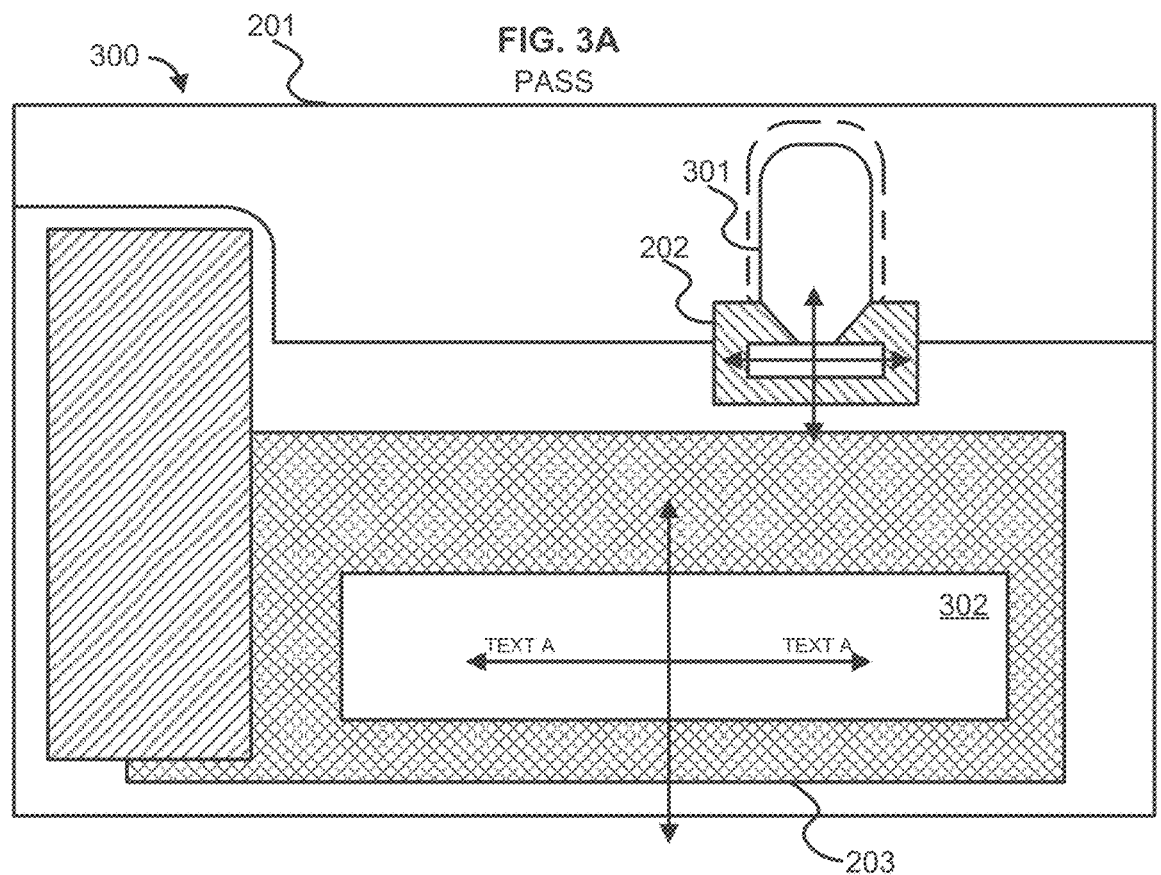
FIG. 3A is an example image of an object.
Figure 3B:
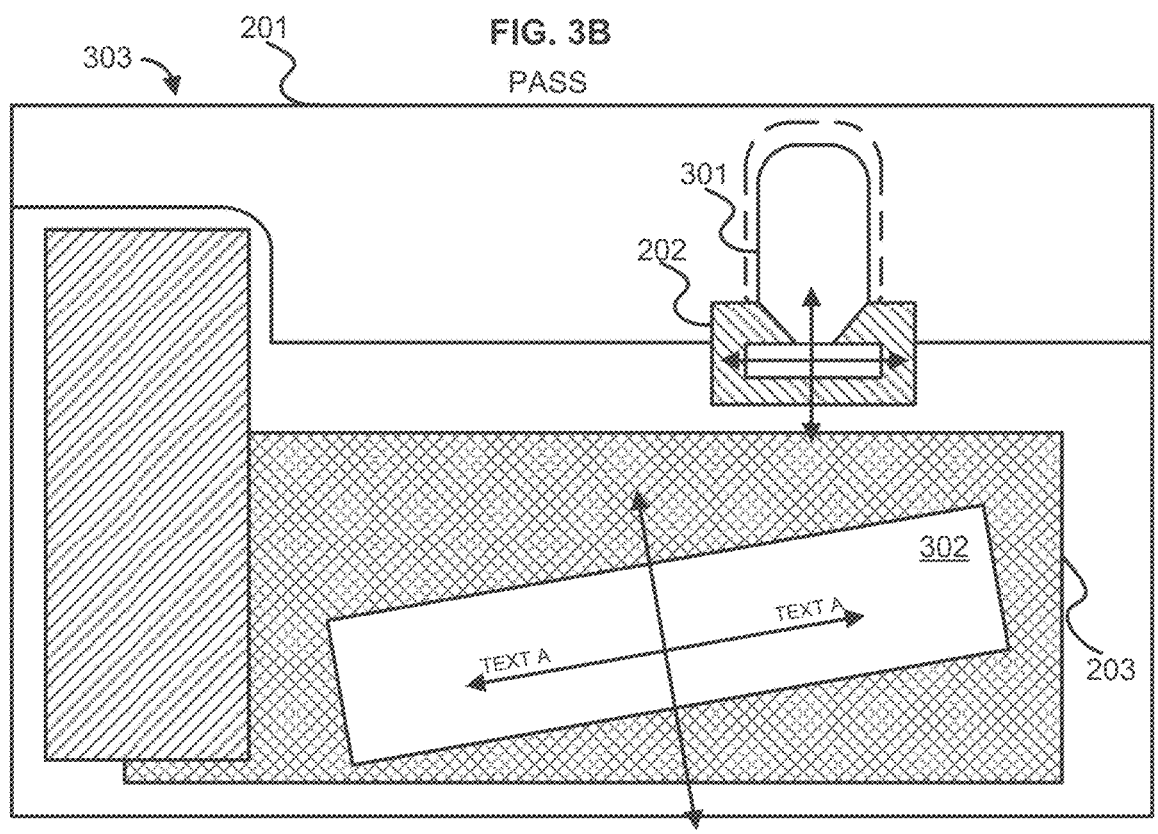
FIG. 3B is an example image of an object.

FIG. 3A and FIG. 3B illustrate an example image 300 and 303 of a tray 201 that comprises an item 301 and an item 302. The item 301 can be a vial and the item 302 can be a filter needle, for example. Whichever of the camera 106, the camera 107, and/or the camera 108 that generates the image 300 can determine that a vial cap is present in the region 202. The presence of a single vial cap indicates that the item 301 is present. The camera 106, the camera 107, and/or the camera 108 that generates the image 300 can determine that, in the region 203, two occurrences of a pattern are present, "TEXT A". In an aspect, the two occurrences of the pattern, "TEXT A", can indicate that a one or more than one instance of the item 302 is present and the camera 106, the camera 107, and/or the camera 108 can generate a PASS or a FAIL signal as appropriate. In another aspect, depending on pattern configuration on the item 302 (e.g., a single instance of the item 302 can have either a single occurrence of "TEXT A" or a double occurrence of "TEXT A") the camera 106, the camera 107, and/or the camera 108 can determine whether "TEXT A" and "TEXT A" appear on the same axis. If "TEXT A" and "TEXT A" appear on the same axis then the camera 106, the camera 107, and/or the camera 108 can determine that a single instance of the item 302 is present and the camera 106, the camera 107, and/or the camera 108 can generate a PASS or a FAIL signal as appropriate. If "TEXT A" and "TEXT A" appear on different axes then the camera 106, the camera 107, and/or the camera 108 can determine that a more than one instance of the item 302 is present and the camera 106, the camera 107, and/or the camera 108 can generate a PASS or a FAIL signal as appropriate. In an aspect, the determination of axes can be used to confirm that any number of the item 302 are present and generate a PASS or a FAIL signal based on the expected number of instances of the item 302 versus the determined number of instances of the item 302.

Figure 4A:
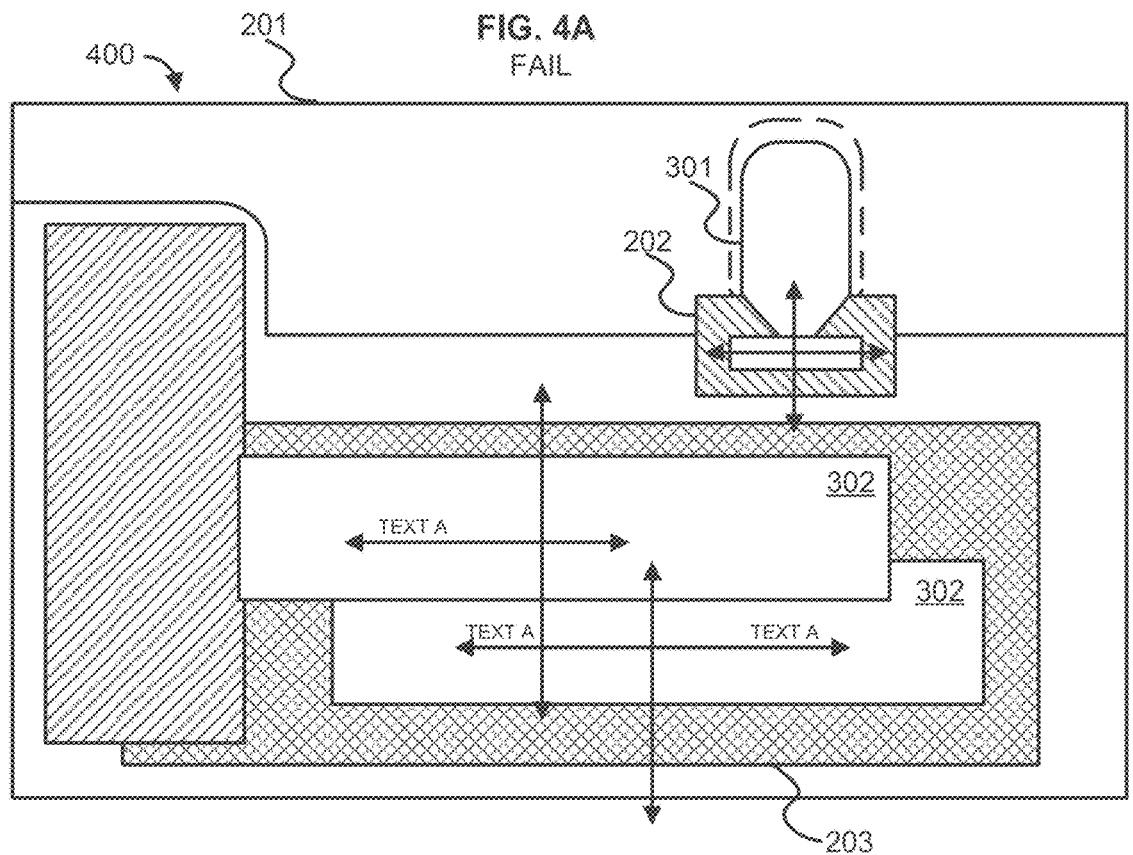
FIG. 4A is an example image of an object.

FIG. 4A illustrates an example image 400 of the tray 201 that comprises the item 301 and two instances of the item 302. The camera 106, the camera 107, and/or the camera 108 that generates the image 400 can determine that, in the region 203, three occurrences of a pattern are present, ("TEXT A"). In an aspect, the three occurrences of the pattern, "TEXT A" can indicate that one or more than one instance of the item 302 is present and the camera 106, the camera 107, and/or the camera 108 can generate a PASS or a FAIL signal as appropriate. In another aspect, depending on pattern configuration on the item 302 (e.g., a single instance of the item 302 can have a single occurrence of "TEXT A", a double occurrence of "TEXT A", or a triple occurrence of "TEXT A") the camera 106, the camera 107, and/or the camera 108 can determine whether the three occurrences of "TEXT A" appear on the same axis. As shown in FIG. 4A, two occurrences of "TEXT A" appear on the same axis and one occurrence of "TEXT A" appears on a different axis. Accordingly, the camera 106, the camera 107, and/or the camera 108 can determine that more than one instance of the item 302 is present and the camera 106, the camera 107, and/or the camera 108 can generate a PASS or a FAIL signal as appropriate. In an aspect, the determination of axes can be used to confirm that any number of the item 302 are present and generate a PASS or a FAIL signal based on the expected number of instances of the item 302 versus the determined number of instances of the item 302.

Figure 4B:
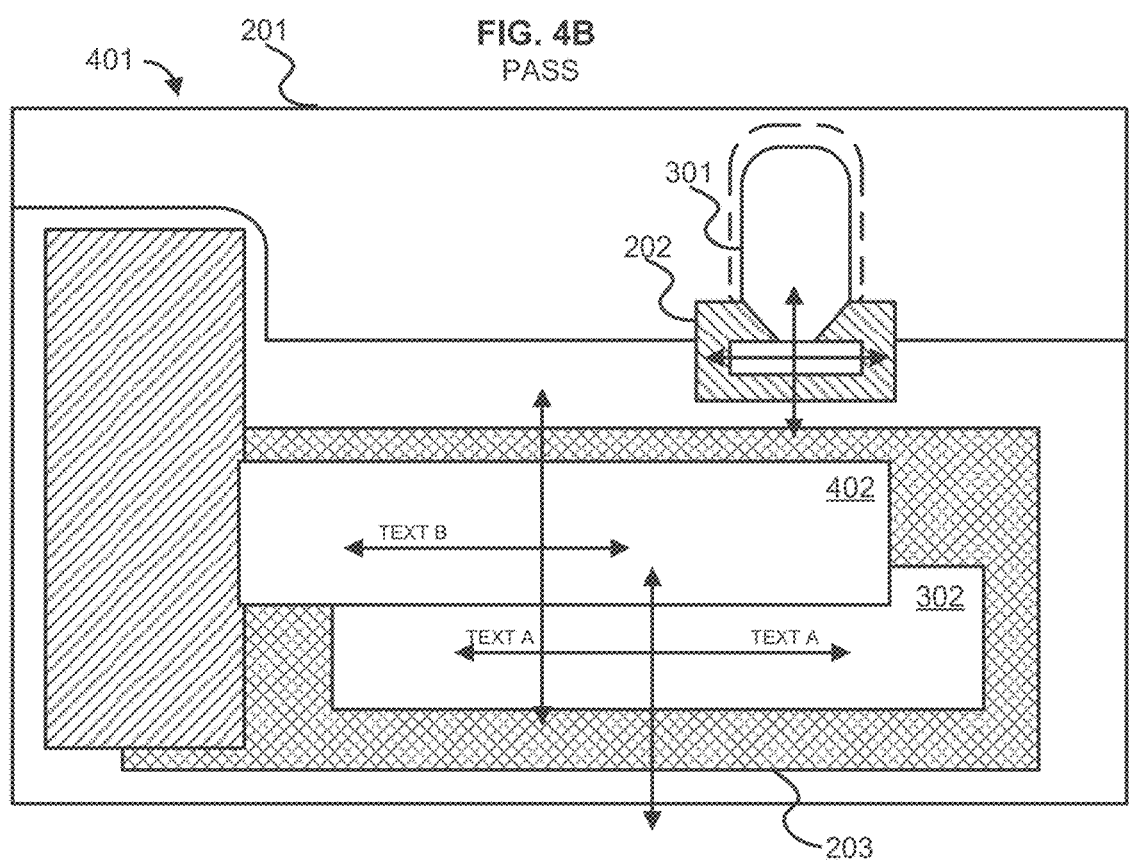
FIG. 4B is an example image of an object.

FIG. 4B illustrates an example image 401 of the tray 201 that comprises the item 301, one instance of the item 302, and one instance of an item 402. In one aspect, the camera 106, the camera 107, and/or the camera 108 that generates the image 400 can determine that, in the region 203, two occurrences of a first pattern are present, ("TEXT A") and one occurrence of a second pattern is present, ("TEXT B"). In an aspect, the two occurrences of the pattern, "TEXT A" can indicate that one or more than one instance of the item 302 is present and the camera 106, the camera 107, and/or the camera 108 can generate a PASS or a FAIL signal as appropriate. In another aspect, depending on pattern configuration on the item 302 (e.g., a single instance of the item 302 can have a single occurrence of "TEXT A", a double occurrence of "TEXT A", or a triple occurrence of "TEXT A") the camera 106, the camera 107, and/or the camera 108 can determine whether the two occurrences of "TEXT A" appear on the same axis. As shown in FIG. 4B, the two occurrences of "TEXT A" appear on the same axis. Accordingly, the camera 106, the camera 107, and/or the camera 108 can determine that more one instance of the item 302 is present and the camera 106, the camera 107, and/or the camera 108 can generate a PASS or a FAIL signal as appropriate. However, the one occurrence of the pattern "TEXT B" can indicate that an item has been placed in the tray 201 that should not be in the tray 201 at this stage in the assembly process. Accordingly, the camera 106, the camera 107, and/or the camera 108 can generate a FAIL signal based on the presence of a pattern that is not intended to be present.

In another aspect, the camera 106, the camera 107, and/or the camera 108 that generates the image 400 can determine that the pattern "TEXT B" is present and can ignore the presence of the pattern "TEXT A" (or any other pattern as required). In an aspect, the one occurrence of the pattern, "TEXT B" can indicate that one instance of the item 302 is present and the camera 106, the camera 107, and/or the camera 108 can generate a PASS signal.

Figure 5A:
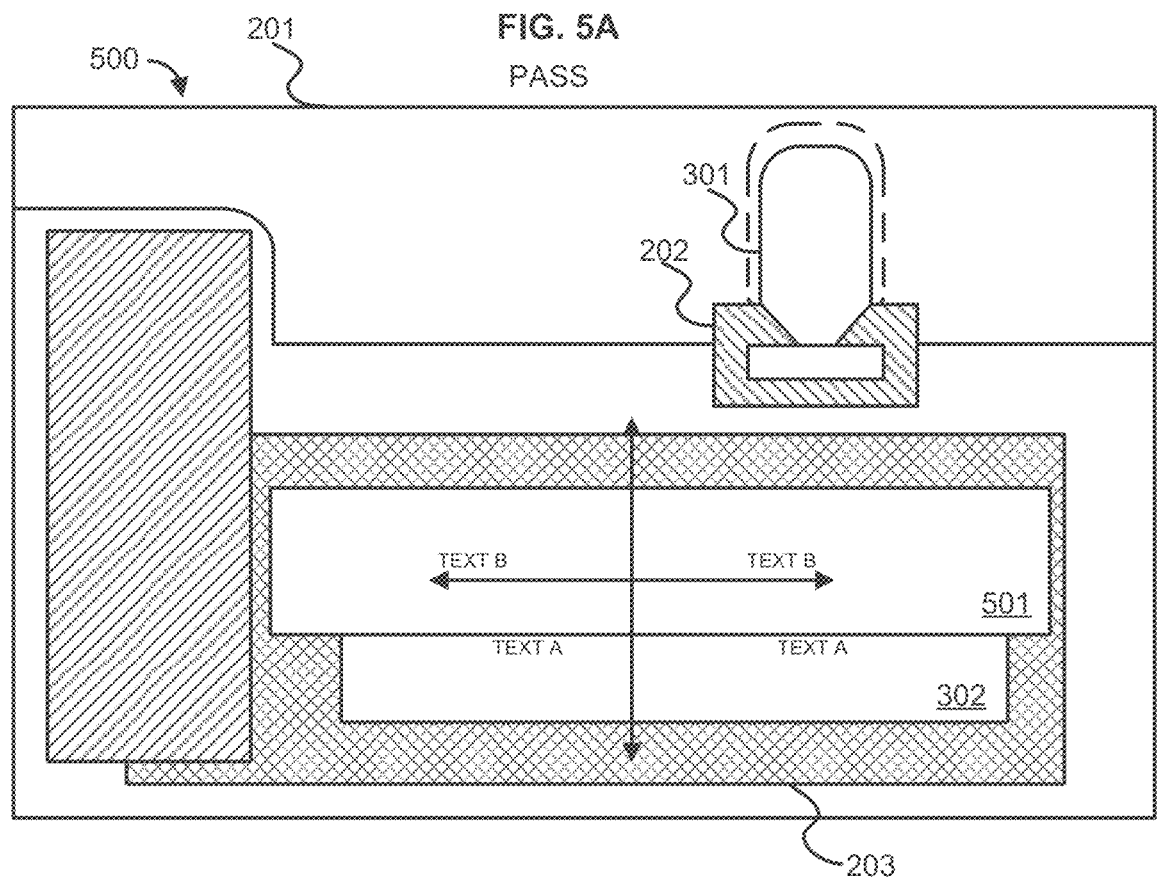
FIG. 5A is an example image of an object.
Figure 5B:
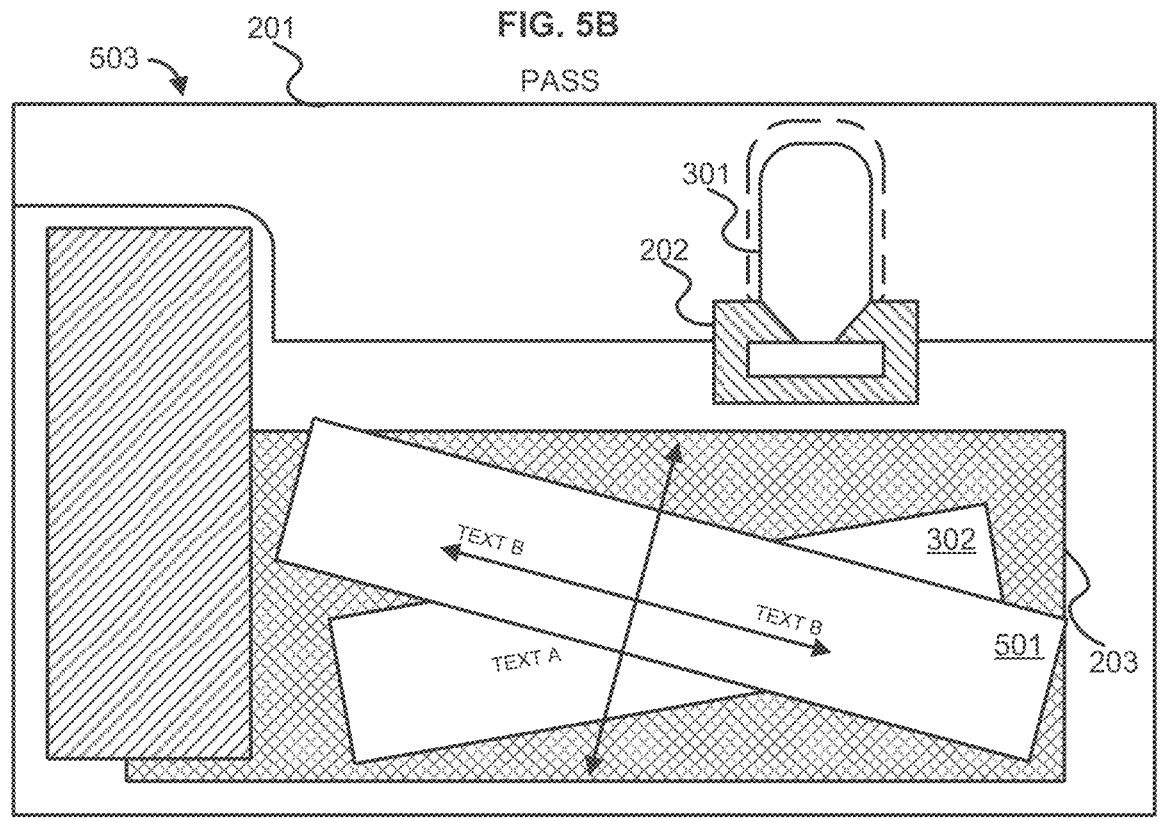
FIG. 5B is an example image of an object.

FIG. 5A illustrates an example image 500 of the tray 201 that comprises the item 301, the item 302, and a single instance of an item 501. The camera 106, the camera 107, and/or the camera 108 that generates the image 500 can be configured to ignore the vial cap in the region 202 and to ignore the presence of the pattern "TEXT A" in the region 203. Instead, the camera 106, the camera 107, and/or the camera 108 that generates the image 400 can determine that, in the region 203, two occurrences of another pattern are present, ("TEXT B"). In an aspect, the two occurrences of the pattern, "TEXT B" can indicate that either one or more than one instance of the item 501 is present and the camera 106, the camera 107, and/or the camera 108 can generate a PASS or a FAIL signal as appropriate. In another aspect, depending on pattern configuration on the item 501 (e.g., a single instance of the item 501 can have a single occurrence of "TEXT B", a double occurrence of "TEXT B", or a triple occurrence of "TEXT B") the camera 106, the camera 107, and/or the camera 108 can determine whether the two occurrences of "TEXT B" appear on the same axis. As shown in FIG. 5A, the two occurrences of "TEXT B" appear on the same axis. Accordingly, the camera 106, the camera 107, and/or the camera 108 can determine that one instance of the item 501 is present and the camera 106, the camera 107, and/or the camera 108 can generate a PASS or a FAIL signal as appropriate. In an aspect, the determination of axes can be used to confirm that any number of the item 501 are present and generate a PASS or a FAIL signal based on the expected number of instances of the item 501 versus the determined number of instances of the item 501. FIG. 5B illustrates an example image 503 of the tray 201 that comprises the item 301, the item 302, and a single instance of the item 501. FIG. 5B is similar to FIG. 5A with the exception that FIG. 5B illustrates that the pattern "TEXT B" occurs twice along the same axis, however at a different angle than the axis in FIG. 5A.

Figure 6A:
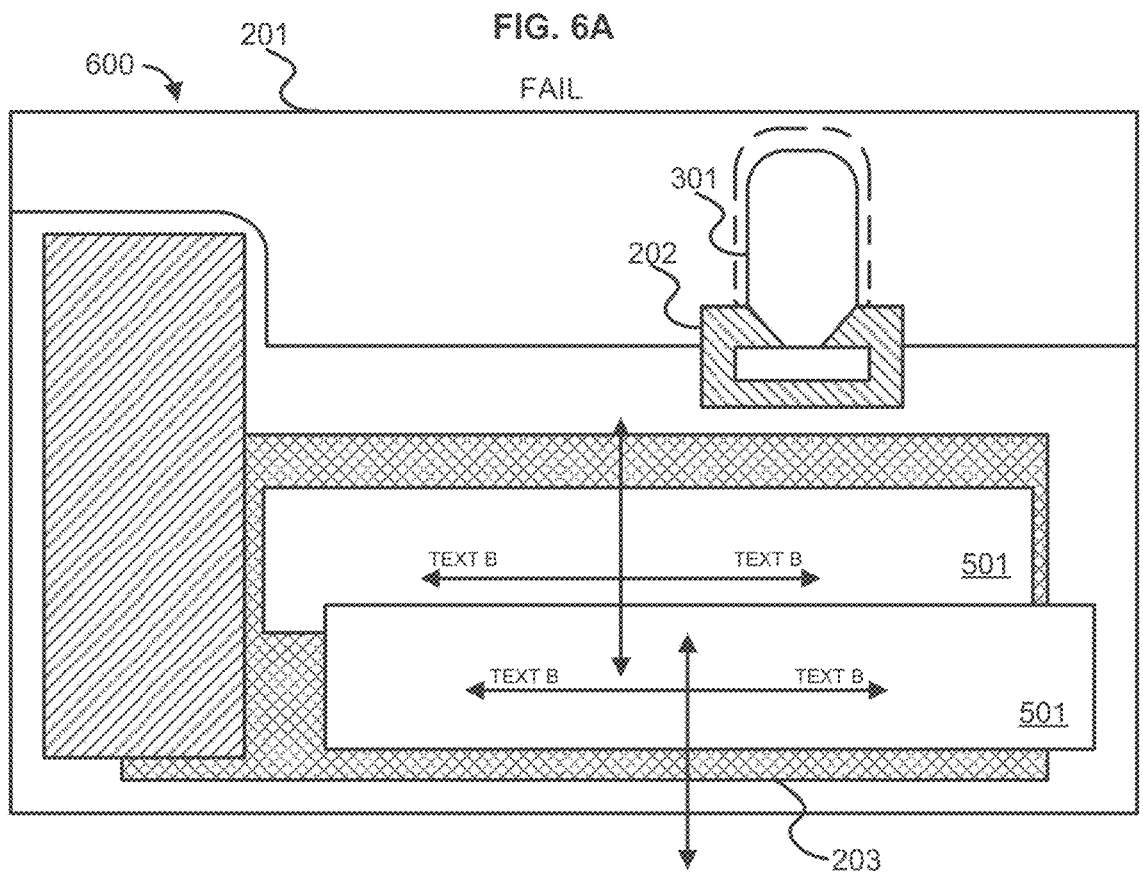
FIG. 6A is an example image of an object.

FIG. 6A illustrates an example image 600 of the tray 201 that comprises the item 301 and two instances of the item 501. The camera 106, the camera 107, and/or the camera 108 that generates the image 600 can determine that, in the region 203, four occurrences of a pattern are present, "TEXT B". In an aspect, the four occurrences of the pattern, "TEXT B" can indicate that one or more than one instance of the item 501 is present and the camera 106, the camera 107, and/or the camera 108 can generate a PASS or a FAIL signal as appropriate. In another aspect, depending on pattern configuration on the item 501 (e.g., a single instance of the item 501 can have a single occurrence of "TEXT B", a double occurrence of "TEXT B", a triple occurrence of "TEXT B", or a quadruple occurrence of "TEXT B") the camera 106, the camera 107, and/or the camera 108 can determine the axes upon which the four occurrences of "TEXT B" appear. As shown in FIG. 5A, two occurrences of "TEXT B" appear on a first axis and the other two occurrences of "TEXT B" appear on a second axis. Accordingly, as the two sets of "TEXT B" appear on different axes, the camera 106, the camera 107, and/or the camera 108 can determine that more than one instance of the item 501 is present and the camera 106, the camera 107, and/or the camera 108 can generate a PASS or a FAIL signal as appropriate. In an aspect, the determination of axes can be used to confirm that any number of the item 501 are present and generate a PASS or a FAIL signal based on the expected number of instances of the item 501 versus the determined number of instances of the item 501.

Figure 6B:
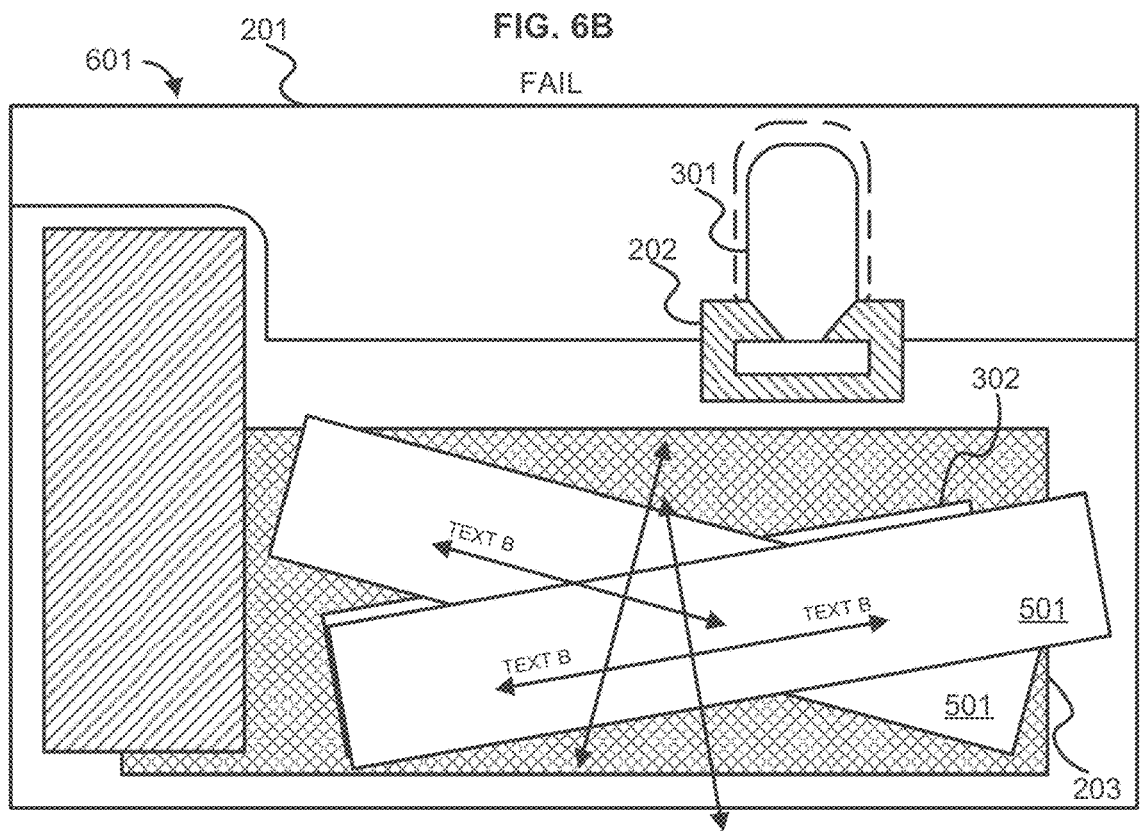
FIG. 6B is an example image of an object.

FIG. 6B illustrates an example image 601 of the tray 201 that comprises the item 301, the item 302, and two instances of the item 501. The camera 106, the camera 107, and/or the camera 108 that generates the image 601 can determine that, in the region 203, three occurrences of a pattern are present, "TEXT B". In an aspect, the three occurrences of the pattern, "TEXT B" can indicate that one or more than one instance of the item 501 is present and the camera 106, the camera 107, and/or the camera 108 can generate a PASS or a FAIL signal as appropriate. In another aspect, depending on pattern configuration on the item 501 (e.g., a single instance of the item 501 can have a single occurrence of "TEXT B", a double occurrence of "TEXT B", a triple occurrence of "TEXT B", or a quadruple occurrence of "TEXT B") the camera 106, the camera 107, and/or the camera 108 can determine the axes upon which the three occurrences of "TEXT B" appear. As shown in FIG. 6B, two occurrences of "TEXT B" appear on a first axis and the one occurrence of "TEXT B" appears on a second axis. Accordingly, as the two sets of "TEXT B" appear on different axes, the camera 106, the camera 107, and/or the camera 108 can determine that more than one instance of the item 501 is present and the camera 106, the camera 107, and/or the camera 108 can generate a PASS or a FAIL signal as appropriate. In an aspect, the determination of axes can be used to confirm that any number of the item 501 are present and generate a PASS or a FAIL signal based on the expected number of instances of the item 501 versus the determined number of instances of the item 501.

Figure 7A:
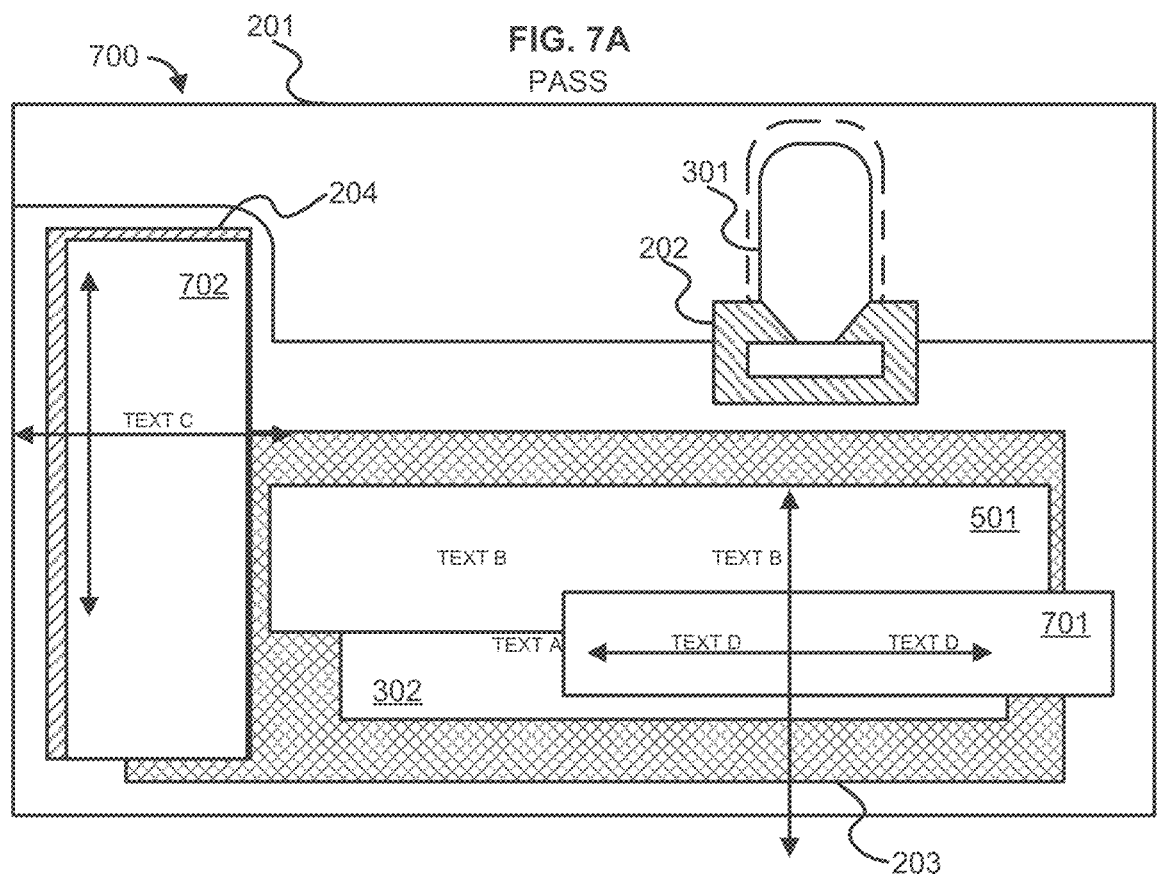
FIG. 7A is an example image of an object.
Figure 7B:
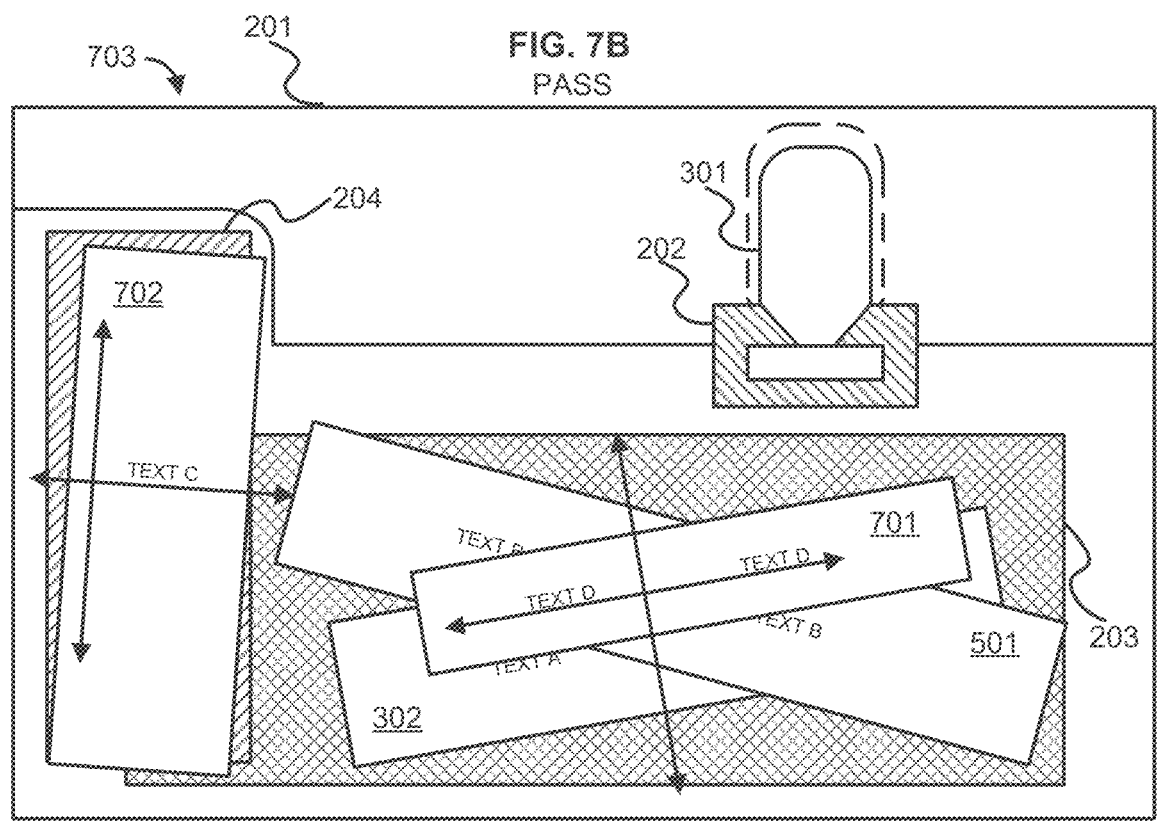
FIG. 7B is an example image of an object.

FIG. 7A illustrates an example image 700 of the tray 201 that comprises the item 301, the item 302, the item 501, a single instance of an item 701, and a single instance of an item 702. The camera 106, the camera 107, and/or the camera 108 that generates the image 700 can be configured to ignore the vial cap in the region 202 and to ignore the presence of the patterns "TEXT A" and "TEXT B" in the region 203. Instead, the camera 106, the camera 107, and/or the camera 108 that generates the image 700 can determine that, in the region 203, two occurrences of another pattern are present, ("TEXT D"). In an aspect, the two occurrences of the pattern, "TEXT D" can indicate that either one or more than one instance of the item 701 is present and the camera 106, the camera 107, and/or the camera 108 can generate a PASS or a FAIL signal as appropriate. In another aspect, depending on pattern configuration on the item 701 (e.g., a single instance of the item 701 can have a single occurrence of "TEXT D", a double occurrence of "TEXT D", or a triple occurrence of "TEXT D") the camera 106, the camera 107, and/or the camera 108 can determine whether the two occurrences of "TEXT D" appear on the same axis. As shown in FIG. 7A, the two occurrences of "TEXT D" appear on the same axis. Accordingly, the camera 106, the camera 107, and/or the camera 108 can determine that one instance of the item 701 is present and the camera 106, the camera 107, and/or the camera 108 can generate a PASS or a FAIL signal as appropriate. In an aspect, the determination of axes can be used to confirm that any number of the item 701 are present and generate a PASS or a FAIL signal based on the expected number of instances of the item 701 versus the determined number of instances of the item 701. In the same image 700, the camera 106, the camera 107, and/or the camera 108 can determine that, in the region 204, two occurrences of another pattern are present, ("TEXT C"). In an aspect, the two occurrences of the pattern, "TEXT C" can indicate that either one or more than one instance of the item 702 is present and the camera 106, the camera 107, and/or the camera 108 can generate a PASS or a FAIL signal as appropriate. In another aspect, depending on pattern configuration on the item 702 (e.g., a single instance of the item 702 can have a single occurrence of "TEXT C", a double occurrence of "TEXT C", or a triple occurrence of "TEXT C") the camera 106, the camera 107, and/or the camera 108 can determine whether the two occurrences of "TEXT C" appear on the same axis. As shown in FIG. 7A, the two occurrences of "TEXT C" appear on the same axis. Accordingly, the camera 106, the camera 107, and/or the camera 108 can determine that one instance of the item 702 is present and the camera 106, the camera 107, and/or the camera 108 can generate a PASS or a FAIL signal as appropriate. In an aspect, the determination of axes can be used to confirm that any number of the item 702 are present and generate a PASS or a FAIL signal based on the expected number of instances of the item 702 versus the determined number of instances of the item 702. FIG. 7B illustrates an example image 703 of the tray 201 that comprises the item 301, the item 302, the item 501, a single instance of the item 701, and a single instance of the item 702. FIG. 7B is similar to FIG. 7A with the exception that FIG. 7B illustrates that the pattern "TEXT D" occurs twice along the same axis, however at a different angle than the axis in FIG. 7A and similarly the pattern "TEXT C" occurs twice along the same axis, however at a different angle than the axis in FIG. 7A.

Figure 8A:
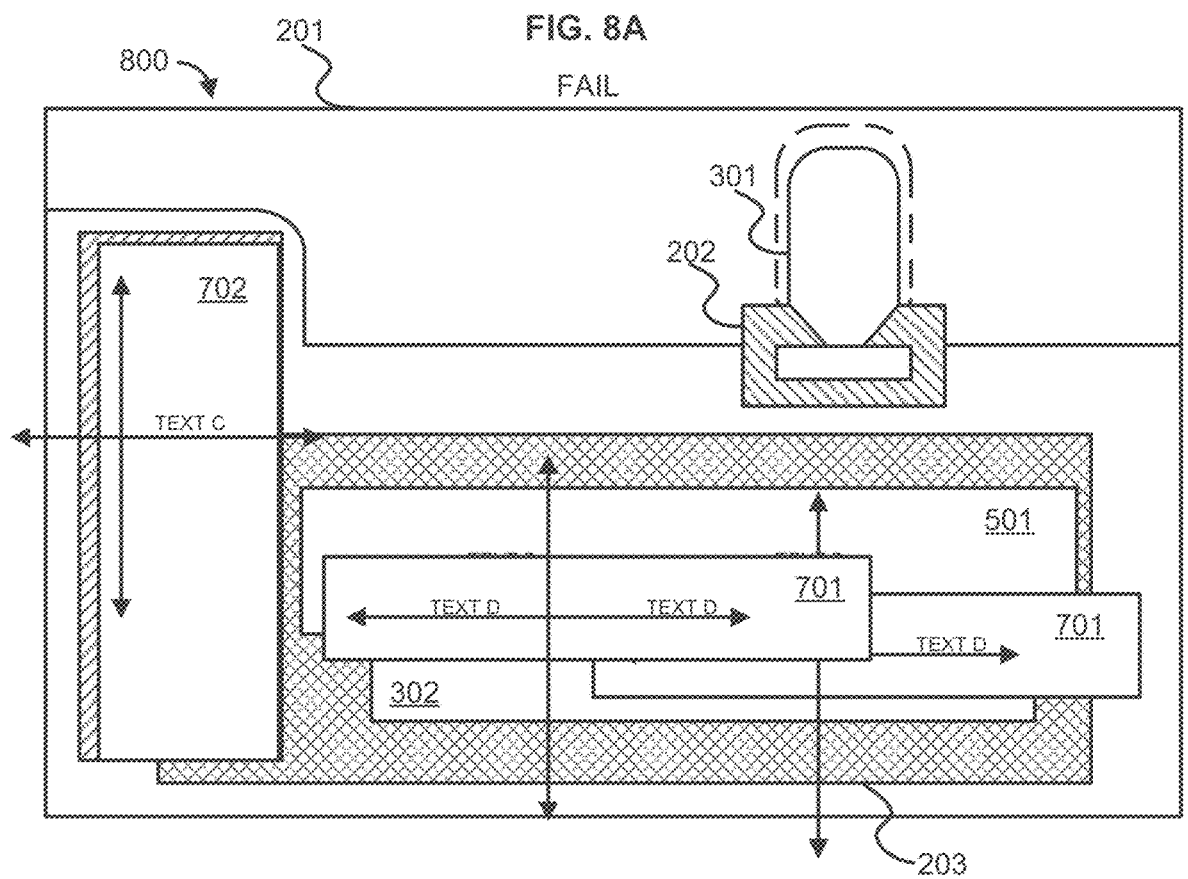
FIG. 8A is an example image of an object.
Figure 8B:
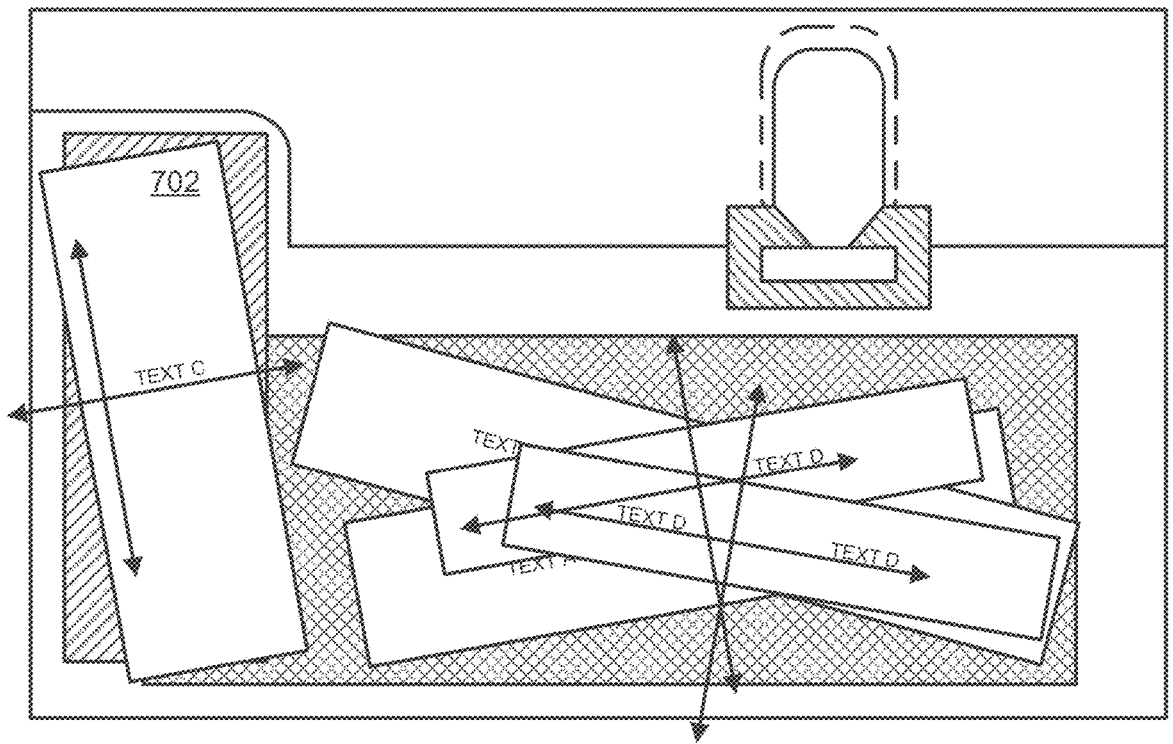
FIG. 8B is an example image of an object.

FIG. 8A illustrates an example image 800 of the tray 201 that comprises the item 301, the item 302, the item 501, two instances of the item 701, and a single instance of the item 702. The camera 106, the camera 107, and/or the camera 108 that generates the image 800 can determine that, in the region 203, three occurrences of a pattern are present, "TEXT D". In an aspect, the three occurrences of the pattern, "TEXT D" can indicate that one or more than one instance of the item 701 is present and the camera 106, the camera 107, and/or the camera 108 can generate a PASS or a FAIL signal as appropriate. In another aspect, depending on pattern configuration on the item 701 (e.g., a single instance of the item 701 can have a single occurrence of "TEXT D", a double occurrence of "TEXT D", a triple occurrence of "TEXT D", or a quadruple occurrence of "TEXT D") the camera 106, the camera 107, and/or the camera 108 can determine the axes upon which the three occurrences of "TEXT D" appear. As shown in FIG. 8A, two occurrences of "TEXT D" appear on a first axis and the one occurrence of "TEXT D" appears on a second axis. Accordingly, as the two sets of "TEXT D" appear on different axes, the camera 106, the camera 107, and/or the camera 108 can determine that more than one instance of the item 701 is present and the camera 106, the camera 107, and/or the camera 108 can generate a PASS or a FAIL signal as appropriate. In an aspect, the determination of axes can be used to confirm that any number of the item 701 are present and generate a PASS or a FAIL signal based on the expected number of instances of the item 701 versus the determined number of instances of the item 701. FIG. 8B is similar to FIG. 8A with the exception that FIG. 8B illustrates that the pattern "TEXT D" occurs twice along a first axis and once along a second axis, however the first and second axes are at different angles than the axes in FIG. 8A.

Returning to FIG. 1, each of the camera 106, the camera 107, and the camera 108 can independently determine both the presence or the absence of one or more patterns in an image and determine a rotation of each the one or more patterns in the image of an object 104. Each of the camera 106, the camera 107, and the camera 108 can perform an action based on the presence or absence and the rotation of the one or more patterns in the image. If a camera determines that a correct number of an item is present in the image of an object 104 based on presence of pattern and rotation of the pattern, the action can comprise transmitting a PASS signal to the pass/fail controller 113. If the camera determines that an incorrect number of an item is present in the image of an object 104 based on presence of pattern and rotation of the pattern, the action can comprise transmitting a FAIL signal to the pass/fail controller 113. If each of the camera 106, the camera 107, and/or the camera 108 issues a PASS signal to the pass/fail controller 113, then the pass/fail controller 113 can provide a signal to the PLC 112 to cause the stepper motor 105 to advance the conveyor belt 101 to advance the one or more objects 104 to be positioned under the field of view of the next camera. The pass/fail controller 113 can further transmit a notification to each of the monitors 114-116 to display a PASS notification. If one or more of the camera 106, the camera 107, and/or the camera 108 issues a FAIL signal to the pass/fail controller 113, the pass/fail controller 113 will not provide a signal to the PLC 112 to cause the stepper motor 105 to advance. The pass/fail controller 113 can further transmit a notification to the monitors 114-116 associated with the camera(s) issuing the FAIL signal to display a FAIL notification. An operator (e.g., a human or a robot) positioned at the monitors 114-116 displaying the FAIL notification can take corrective action to remedy the FAIL status.

In another aspect, one or more of the camera 106, the camera 107, and the camera 108 can count a number of the one or more objects 104. For example, a the one or more objects 104 pass by one of the camera 106, the camera 107, and the camera 108, the camera can increment a tally of the one or more objects 104 imaged by the camera. In a further aspect, a number of empty locations can be interspersed between the one or more objects 104. For example, in certain scenarios one or more of the camera 106, the camera 107, and the camera 108 may not have an object 104 within a respective field of view. The conveyor belt 101 can have a pattern (e.g., a "no tray" pattern) embodied thereon in a position where the object 104 would otherwise be placed. The camera 106, the camera 107, and the camera 108 can identify the pattern and issue a PASS signal to contribute to advancement of the conveyor belt 101.

Figure 9:
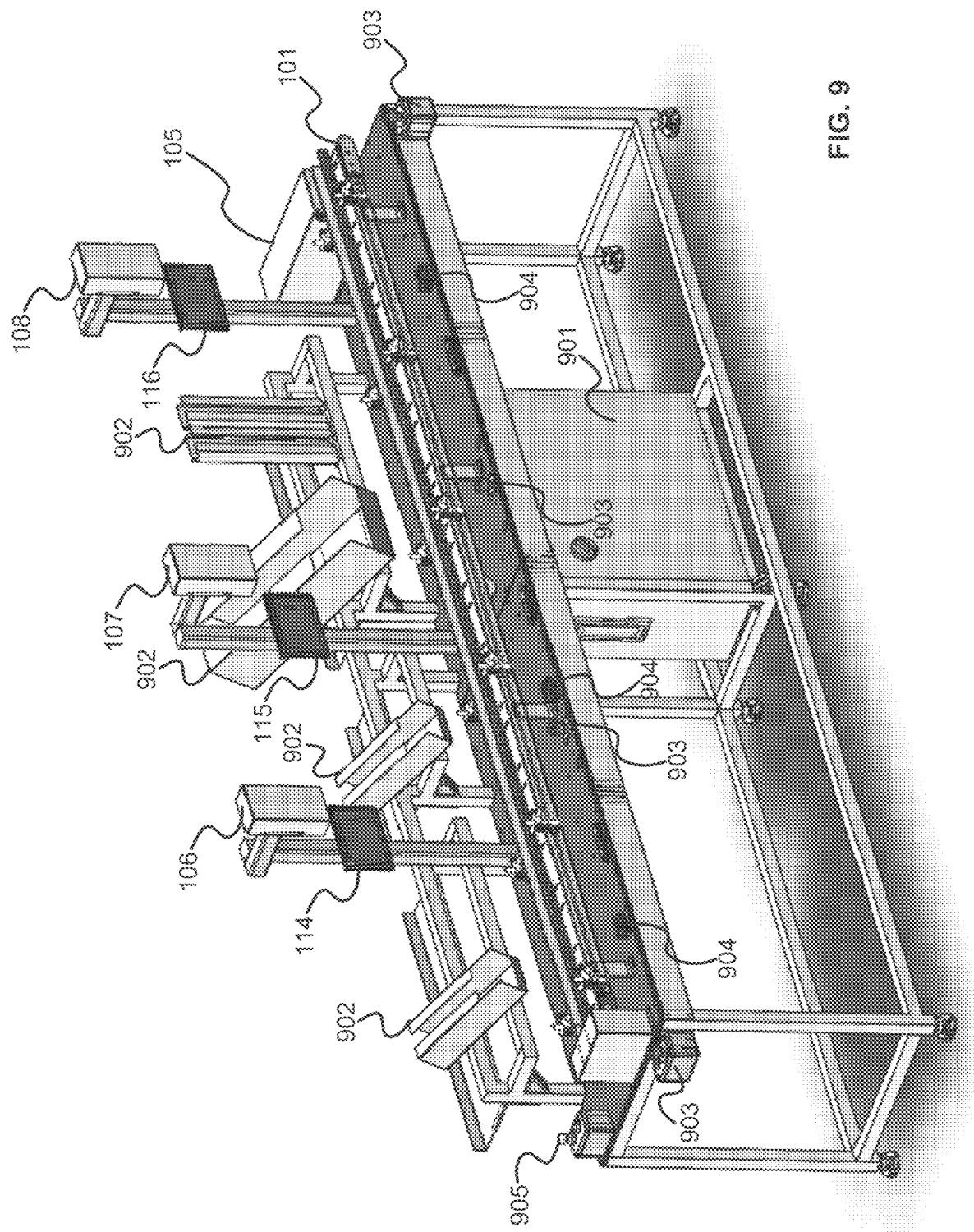
FIG. 9 is an example embodiment of an example system.

FIG. 9 illustrates an example embodiment of the system 100 illustrating positioning of camera 106, the camera 107, and the camera 108 relative to the conveyor belt 101. FIG. 9 further illustrates positioning of the monitors 114-116. The stepper motor 105 is illustrated at one end of the conveyor belt 101. One or more of the PLC 112 and/or the pass/fail controller 113 can be contained with a housing 901. One or more dispensers 902 can be configured for storing one or more items to be accessed during assembly into the one or more objects 104. The system 100 can comprise one or more emergency stop ("E-Stop") buttons 903. The E-Stop buttons 903 can be engaged at any point in time to temporarily cease operation of the system 100, for any reason. The E-Stop buttons 903 can be reset, and the system 100 restarted (e.g., by an operator or technician that has determined that it is safe to do so). The system 100 can comprise one or more OptoSwitches 904. The OptoSwitches 904 can be actuated ("tripped") by placing a finger or thumb in the saddle-like structure of the OptoSwitch 904. This action breaks an optical signal path, causing a switch condition. The OptoSwitches 904 can be used to accept a visual inspection during "Manual Trigger" mode, and start/restart the belt motion during "Autonomous" (or "Auto") mode.

The system 100 can comprise a key switch mechanism 905. The key switch mechanism 905 can be used to toggle between an "Autonomous" Mode and "Manual Trigger" Mode. Under normal operation, regardless of mode, a first operator station can comprise an operator loading trays onto the conveyor belt 101. In an aspect, these trays can be pre-fitted with a prefilled capped vial. In manual trigger mode, at a second operator station, an operator can load a filter needle tip into the tray. After this operation, the camera 106 inspects the tray for the appropriate items. At a third operator station, an injection needle tip can be added to the tray. Then, the camera 107 inspects the tray for appropriate items. At a fourth operator station, an operator loads an empty blister-packed syringe into the tray. Afterwards, a fifth operator loads a Physician Insert (PI) into the tray. After the PI is loaded, the camera 108 inspects the tray for completed loading. Once the tray passes this last station, the fully populated tray exits the conveyor belt 101 for boxing.

In automated mode, trays are moved down the conveyor belt 101 automatically. The system 100 can maintain a dwell time (e.g., 1-5 seconds) before the conveyor belt 101 shifts to the next position. The shift occurs only when all three inspection cameras (e.g., the camera 106, the camera 107, and the camera 108) clear the tray ("Pass") that is being inspected by a respective camera. An issue at any inspection station can result in a the conveyor belt 101 and a "red light" condition ("Fail"), at which point an operator can correct the issue or pull the tray from the conveyor belt 101 (each camera can allow the conveyor belt 101 to advance when there is no tray in its field of view). The advancement of the conveyor belt 101 can be dependent on all cameras detecting a "passing" tray configuration. A display screen (e.g., the monitors 114-116) at each camera station can display the associated camera's video stream, with overlaid "Pass", "Fail", or "No Job" statuses depending on the inspection results. Camera online status can be reset from the monitors 114-116 if required during operation.

Figure 10:
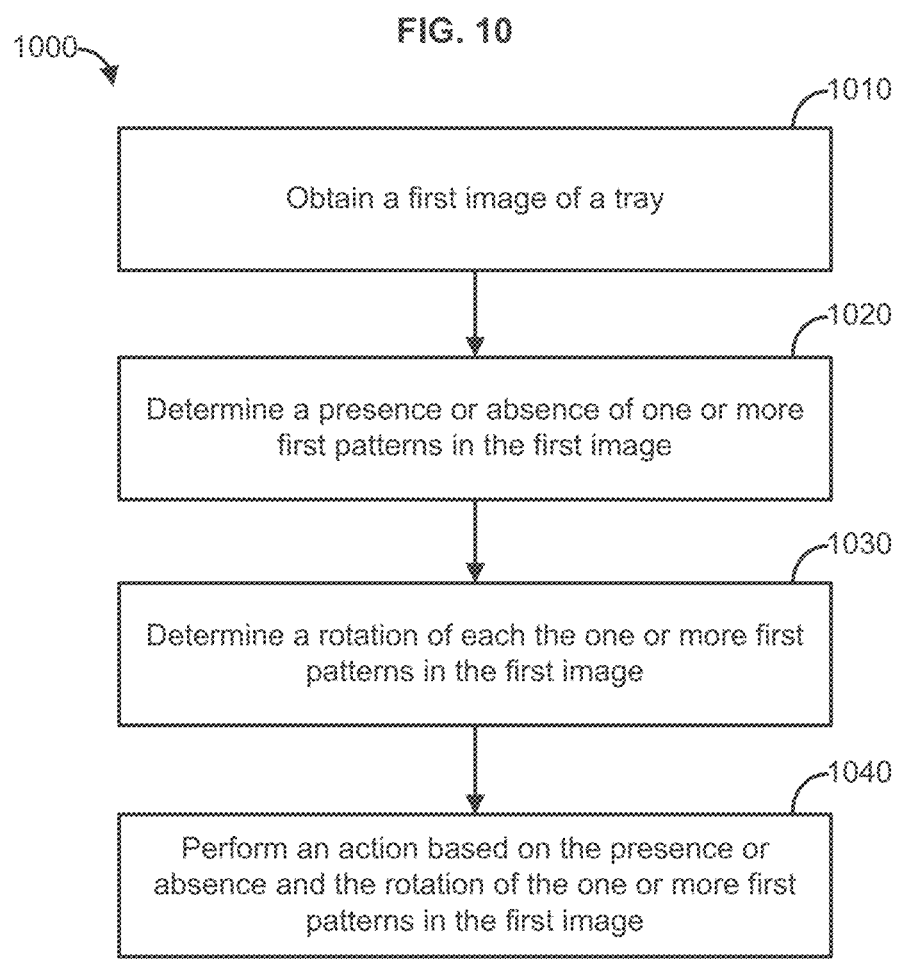
FIG. 10 is a flowchart illustrating an example method.

In an aspect, illustrated in FIG. 10, a method 1000 is disclosed comprising obtaining a first image of a tray at 1010. The method 1000 can comprise determining a presence or absence of one or more first patterns in the first image at 1020. The one or more first patterns can comprise text patterns, numeric patterns, symbol patterns, and combinations thereof. The method 1000 can comprise determining a rotation of each the one or more first patterns in the first image at 1030. The method 1000 can comprise performing an action based on the presence or absence and the rotation of the one or more first patterns in the first image at 1040. In an aspect, each step of the method 1000 can be performed by a computing device, a camera (with processing functionality), or a combination thereof. In some aspect, multiple computing devices and/or cameras can be employed to perform the method 1000. For example, multiple cameras can be used wherein a first camera can perform steps 1010, 1020, and step 1030 while a second camera performs step 1040. In another aspect, the method 1000 can be repeated at each of several cameras and/or computing devices as a tray proceeds along an assembly line. For example, steps 1010, 1020, 1030, and 1040 can be performed by a first camera for a specific pattern(s), then steps 1010, 1020, 1030, and 1040 can be performed again by a second camera for another specific pattern(s). Still further, one or more sub-steps described herein can be performed by a designated camera and/or computing device.

Determining a presence or absence of one or more first patterns in the first image can comprise determining presence of one or two of the one or more first patterns and wherein determining a rotation of each the one or more first patterns in the first image can comprise determining that the one or two of the one or more first patterns are on a first axis. Performing an action based on the presence or absence and the rotation of the one or more first patterns in the first image can comprise generating a pass inspection signal and advancing a belt having the tray disposed thereon. Determining a presence or absence of one or more first patterns in the first image can comprise determining presence of three or more of the one or more first patterns. Performing an action based on the presence or absence and the rotation of the one or more first patterns in the first image can comprise generating a fail inspection signal and notifying an operator that a first item associated with the one or more first patterns should be removed from the tray. Determining a presence or absence of one or more first patterns in the first image can comprise determining presence of two of the one or more first patterns and wherein determining a rotation of each the one or more first patterns in the first image can comprise determining that the two of the one or more first patterns are not on a same axis. Performing an action based on the presence or absence and the rotation of the one or more first patterns in the first image can comprise generating a fail inspection signal and notifying an operator that a first item associated with the one or more first patterns should be removed from the tray.

The method 1000 can further comprise obtaining a second image of the tray, determining a presence or absence of one or more second patterns in the second image, determining a rotation of each the one or more second patterns in the second image, and performing an action based on the presence or absence and the rotation of the one or more second patterns in the second image. The one or more second patterns can comprise text patterns, numeric patterns, symbol patterns, and combinations thereof. Determining a presence or absence of one or more second patterns in the second image can comprise determining presence of one or two of the one or more second patterns and wherein determining a rotation of each the one or more second patterns in the second image can comprise determining that the one or two of the one or more second patterns are on a second axis. Performing an action based on the presence or absence and the rotation of the one or more second patterns in the second image can comprise generating a pass inspection signal and advancing a belt having the tray disposed thereon. Determining a presence or absence of one or more second patterns in the second image can comprise determining presence of three or more of the one or more second patterns. Performing an action based on the presence or absence and the rotation of the one or more second patterns in the second image can comprise generating a fail inspection signal and notifying an operator that a second item associated with the one or more second patterns should be removed from the tray. Determining a presence or absence of one or more second patterns in the second image can comprise determining presence of two of the one or more second patterns and wherein determining a rotation of each the one or more second patterns in the second image can comprise determining that the two of the one or more second patterns are not on a same axis. Performing an action based on the presence or absence and the rotation of the one or more second patterns in the second image can comprise generating a fail inspection signal and notifying an operator that a second item associated with the one or more second patterns should be removed from the tray.

The method 1000 can further comprise determining a location of a cleat in the first image, comparing the determined location of the cleat in the first image to a reference location, determining that the determined location is different from the reference location, determining an offset based on the difference between the determined location and the reference location, and transmitting a signal to a belt controller to adjust a distance to advance a belt having the tray disposed thereon by the offset. The offset can be one of a negative value, a positive value, or a zero value. In an aspect, determining the offset based on the difference between the determined location and the reference location, and transmitting the signal to the belt controller to adjust the distance to advance the belt having the tray disposed thereon by the offset can be performed by one or more cameras. For example, a single camera can be designated to determine the offset. The offset determination can be made after each movement of the belt.

The method 1000 can further comprise repeatedly obtaining a first image of a tray, determining a presence or absence of one or more first patterns in the first image, determining a rotation of each the one or more first patterns in the first image, and performing an action based on the presence or absence and the rotation of the one or more first patterns in the first image for each of a plurality of trays.

The method 1000 can further comprise counting a number of the plurality of trays, wherein a number of empty tray locations are interspersed between the plurality of trays. The method 1000 can further comprise counting a number of the empty tray locations. Determining the presence or absence of one or more first patterns in the first image can comprise determining a no tray pattern. Performing the action based on the presence or absence and the rotation of the one or more second patterns in the first image can comprise advancing a belt having the no tray pattern disposed thereon.

Figure 11:
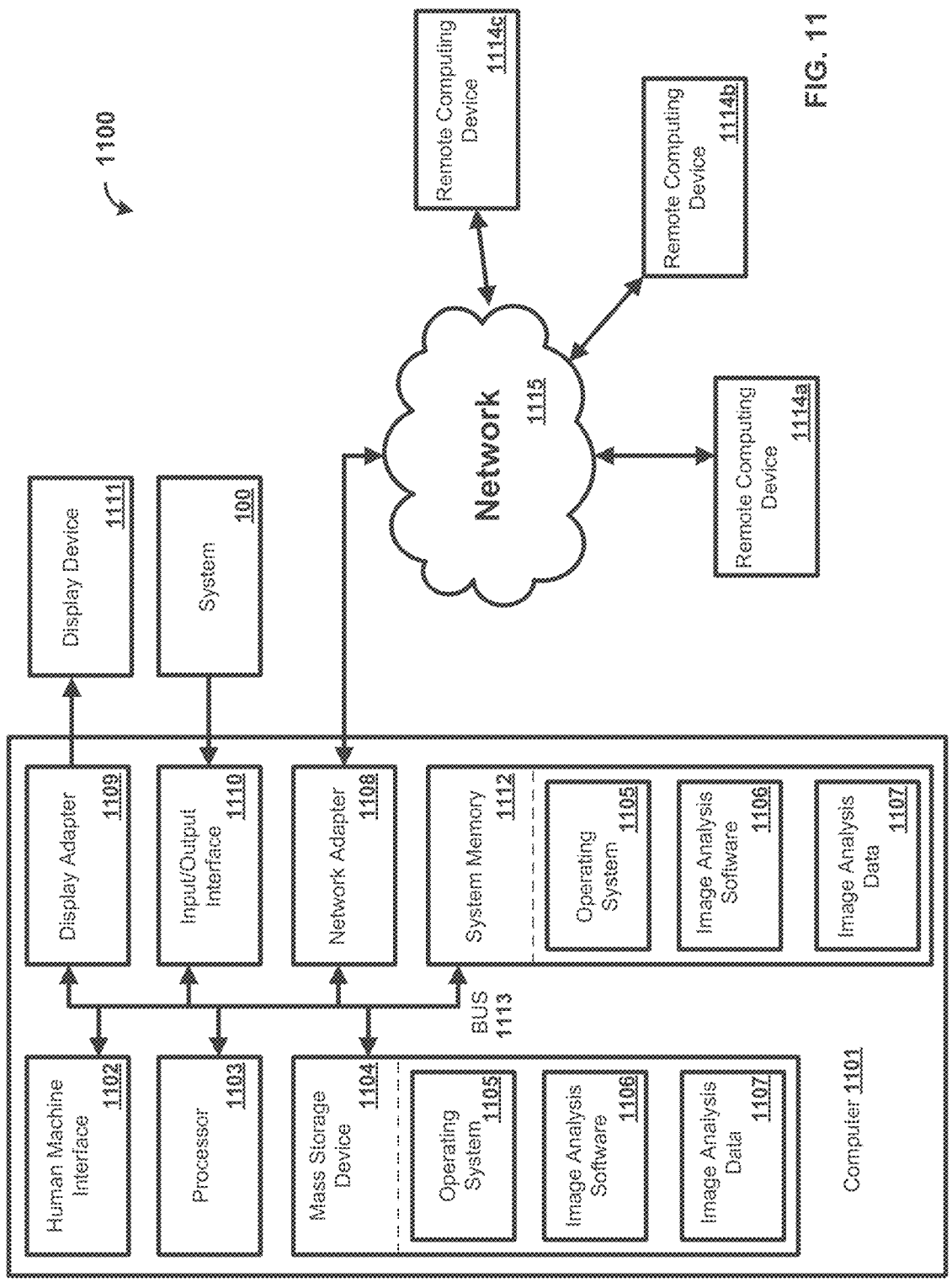
FIG. 11 is an exemplary operating environment.

In an exemplary aspect, the methods and systems can be implemented on a computer 1101 as illustrated in FIG. 11 and described below. By way of example, the camera 106, the camera 107, the camera 108, the PLC 112, and/or the pass/fail controller 113 (or a component thereof) of FIG. 1 can be a computer 1101 as illustrated in FIG. 11. Similarly, the methods and systems disclosed can utilize one or more computers to perform one or more functions in one or more locations. FIG. 2 is a block diagram illustrating an exemplary operating environment 1100 for performing the disclosed methods. This exemplary operating environment 1100 is only an example of an operating environment and is not intended to suggest any limitation as to the scope of use or functionality of operating environment architecture. Neither should the operating environment 1100 be interpreted as having any dependency or requirement relating to any one or combination of components illustrated in the exemplary operating environment 1100.

The present methods and systems can be operational with numerous other general purpose or special purpose computing system environments or configurations. Examples of well known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, programmable logic controllers (PLCs), minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, and/or the like that perform particular tasks or implement particular abstract data types. The disclosed methods can also be practiced in grid-based and distributed computing environments where tasks are performed by remote processing devices that are linked through a communications network. In a distributed computing environment, program modules can be located in local and/or remote computer storage media including memory storage devices.

Further, one skilled in the art will appreciate that the systems and methods disclosed herein can be implemented via a general-purpose computing device in the form of a computer 1101. The computer 1101 can comprise one or more components, such as one or more processors 1103, a system memory 1112, and a bus 1113 that couples various components of the computer 1101 including the one or more processors 1103 to the system memory 1112. In the case of multiple processors 1103, the system can utilize parallel computing.

The bus 1113 can comprise one or more of several possible types of bus structures, such as a memory bus, memory controller, a peripheral bus, an accelerated graphics port, and a processor or local bus using any of a variety of bus architectures. The bus 1113, and all buses specified in this description can also be implemented over a wired or wireless network connection.

The computer 1101 typically comprises a variety of computer readable media. Exemplary readable media can be any available media that is accessible by the computer 1101 and comprises, for example and not meant to be limiting, both volatile and non-volatile media, removable and non-removable media. The system memory 1112 can comprise computer readable media in the form of volatile memory, such as random access memory (RAM), and/or non-volatile memory, such as read only memory (ROM). The system memory 1112 typically can comprise data such as image analysis data 1107 and/or program modules such as operating system 1105 and image analysis software 1106 that are accessible to and/or are operated on by the one or more processors 1103.

In another aspect, the computer 1101 can also comprise other removable/non-removable, volatile/non-volatile computer storage media. The mass storage device 1104 can provide non-volatile storage of computer code, computer readable instructions, data structures, program modules, and other data for the computer 1101. For example, a mass storage device 1104 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 1104, including by way of example, an operating system 1105 and image analysis software 1106. One or more of the operating system 1105 and image analysis software 1106 (or some combination thereof) can comprise elements of the programming and the image analysis software 1106. Image analysis data 1107 can also be stored on the mass storage device 1104. Image analysis data 1107 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple locations within the network 1115.

In another aspect, the user can enter commands and information into the computer 1101 via an input device (not shown). Examples of such input devices comprise, but are not limited to, a keyboard, pointing device (e.g., a computer mouse, remote control), a microphone, a joystick, a scanner, touch-enabled devices such as a touchscreen, tactile input devices such as gloves and other body coverings, motion sensors, and the like. These and other input devices can be connected to the one or more processors 1103 via a human machine interface 1102 that is coupled to the bus 1113, but can be connected by other interface and bus structures, such as, but not limited to, a parallel port, game port, an IEEE 1394 Port (also known as a Firewire port), a serial port, network adapter 1108, and/or a universal serial bus (USB).

In yet another aspect, a display device 1111 can also be connected to the bus 1113 via an interface, such as a display adapter 1109. It is contemplated that the computer 1101 can have more than one display adapter 1109 and the computer 1101 can have more than one display device 1111. For example, a display device 1111 can be a monitor, an LCD (Liquid Crystal Display), light emitting diode (LED) display, television, smart lens, smart glass, and/or a projector. In addition to the display device 1111, other output peripheral devices can comprise components such as speakers (not shown) and a printer (not shown) which can be connected to the computer 1101 via Input/Output Interface 1110. Any step and/or result of the methods can be output in any form to an output device. Such output can be any form of visual representation, including, but not limited to, textual, graphical, animation, audio, tactile, and the like. The display 1111 and computer 1101 can be part of one device, or separate devices.

In an aspect, the computer 1101 can be coupled to the system 100 via the Input/Output Interface 1110. The computer 1101 can be configured to monitor and store data. The computer 1101 can be configured to store images acquired by cameras connected to the system 100, store data related to pass/fail statistics generated during system-generated inspections, etc. The computer 1101 can also be used as a programming interface to one or more smart devices (e.g., smart cameras) and/or embedded logic controllers that require customized firmware to operate. The computer 1101 can be used to generate, troubleshoot, upload, and store iterations of this software or firmware.

The computer 1101 can operate in a networked environment using logical connections to one or more remote computing devices 1114a,b,c. By way of example, a remote computing device 1114a,b,c can be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device or other common network node, and so on. Logical connections between the computer 1101 and a remote computing device 1114a,b,c can be made via a network 1115, such as a local area network (LAN) and/or a general wide area network (WAN). Such network connections can be through a network adapter 1108. A network adapter 1108 can be implemented in both wired and wireless environments. Such networking environments are conventional and commonplace in dwellings, offices, enterprise-wide computer networks, intranets, and the Internet. In an aspect, the network adapter 1108 can be configured to provide power to one or more connected devices (e.g., a camera). For example, the network adapter 1108 can adhere to the Power-over-Ethernet (PoE) standard or the like.

For purposes of illustration, application programs and other executable program components such as the operating system 1105 are illustrated herein as discrete blocks, although it is recognized that such programs and components can reside at various times in different storage components of the computing device 1101, and are executed by the one or more processors 1103 of the computer 1101. An implementation of image analysis software 1106 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" can comprise volatile and non-volatile, removable and non-removable media implemented in any methods or technology for storage of information such as computer readable instructions, data structures, program modules, or other data. Exemplary computer storage media can comprise RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ artificial intelligence (AI) techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

The disclosed methods and systems were implemented, tested, and results compared with a standard manual-only, operator-driven assembly line process. The following table indicates the disclosed methods and systems outperform the standard manual-only, operator-driven assembly line process:

|  | Standard, Manual-Only Process | Assembly Line with Integrated Electronic Visual Inspection | Difference |
| --- | --- | --- | --- |
| Line Rate (units/min) | 11 | 20 | 9 |
| Operators on Line (people) | 25 | 22 | (3.00) |
| Labor cost per carton | $0.46 | $0.23 | ($0.23) |
| Labor Cost @ $12/hour | $10,633.03 | $5,343.44 | ($5,289.59) |
| Overhead @ $3/hour | $106.33 | $60.72 | ($45.61) |
| Cost per Lot | $10,739.36 | $5,404.16 | ($5,335.20) |
| Cost per year (Based on 837,063 units in a year) | $385,048.98 | $192,502.86 | ($192,546.12) |

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method of inspecting one or more objects, the method comprising:
   electronically receiving a first image of a first object, while the first object is stationary and positioned at a first inspection location;
   determining a quantity and/or orientation of one or more first items in the first image;
   comparing a determined quantity and/or orientation of the one or more first items in the first image with an expected quantity and/or orientation of the one or more first items in the first image; and
   providing, with an electronic controller, an electronic instruction enabling the first object to move away from the first inspection location when the determined quantity and/or orientation of the one or more first items in the first image matches the expected quantity and/or orientation of the one or more first items in the first image, wherein, in absence of the electronic instruction, the first object remains stationary until the electronic controller provides another electronic instruction based on 1) a further determination of a quantity and/or orientation of one or more first items in the first image, and 2) a comparison of the further determined quantity and/or orientation of the one or more first items in the first image with the expected quantity and/or orientation of the one or more items in the first image.

2. The method of claim 1, wherein enabling the first object to move away from the first inspection location includes sending the electronic instruction to a moving device, instructing the moving device to convey the first object from the first inspection location.

3. The method of claim 2, wherein the moving device includes a conveyor belt.

4. The method of claim 1, wherein the one or more first items comprise one or more first patterns including text patterns, numeric patterns, and/or symbol patterns.

5. The method of claim 4, wherein receiving the first image of the first object includes receiving the first image from a first imaging device, and wherein determining a quantity and/or orientation of one or more first items in the first image includes determining a presence of two or more of the first patterns within a respective field of view of the first imaging device.

6. The method of claim 5, wherein determining a quantity and/or orientation of one or more first items in the first image includes determining whether the two or more of the first patterns are aligned on a same axis within the respective field of view of the first imaging device, and providing the electronic instruction occurs when the two or more of the first patterns are aligned on the same axis.

7. The method of claim 1, further including prohibiting the first object from moving away from the first inspection location when the determined quantity and/or orientation of the one or more first items in the first image is different from the expected quantity and/or orientation of the one or more first items in the first image.

8. The method of claim 7, further including generating a notification that the determined quantity and/or orientation of the one or more first items in the first image is different from the expected quantity and/or orientation of the one or more first items in the first image.

9. The method of claim 8, further including, after generating the notification, comparing a newly-determined quantity and/or orientation of the one or more first items in the first image with the expected quantity and/or orientation of the one or more first items in the first image, and enabling the first object to move away from the first inspection location when the newly-determined quantity and/or orientation of the one or more first items in the first image matches the expected quantity and/or orientation of the one or more first items in the first image.

10. The method of claim 8, wherein generating the notification causes a machine to take corrective action relative to the first object.

11. The method of claim 10, wherein the corrective action includes adding one or more first items to the first object or removing one or more first items from the first object.

12. The method of claim 1, further including:
    electronically receiving a second image of a second object, while the second object is positioned at a second inspection location spaced apart from the first inspection location;
    determining a quantity and/or orientation of one or more second items in the second image;
    comparing a determined quantity and/or orientation of the one or more second items in the second image with an expected quantity and/or orientation of the one or more second items in the second image; and
    enabling the second object to move away from the second inspection location only when (1) the determined quantity and/or orientation of the one or more first items in the first image matches the expected quantity and/or orientation of the one or more first items in the first image and (2) the determined quantity and/or orientation of the one or more second items in the second image matches the expected quantity and/or orientation of the one or more second items in the second image.

13. The method of claim 12, wherein the one or more first items are identical to the one or more second items.

14. The method of claim 1, wherein the one or more first items include one or more of a syringe, a syringe needle, or an auto-injector.

15. A method, comprising:
    obtaining, with each of a plurality of imagers, a first image;

for each of the plurality of imagers, determining a quantity and/or orientation of one or more first patterns in the first image;

for each of the plurality of imagers, comparing the determined quantity and/or orientation of the one or more first patterns in the first image with an expected quantity and/or orientation of the one or more first patterns;

for each of the plurality of imagers, generating a pass signal or a fail signal based on the comparison; and advancing a belt containing items having the one or more first patterns only when receiving a pass signal for each of the plurality of imagers, wherein the belt is prohibited from moving when a fail signal is received and remains stationary until a pass signal is received from each of the plurality of imagers.

16. The method of claim 15, wherein the one or more first patterns comprise text patterns, numeric patterns, symbol patterns, or combinations thereof.

17. The method of claim 15, wherein the one or more first patterns are positioned on one or more of a syringe, a syringe needle, or an auto-injector.

18. A system comprising:
a movable platform;
an imager configured to:
  obtain an image of a field of view;
  analyze the image to determine a quantity and/or orientation of one or more items within the field of view; and
  generate a pass inspection signal or a fail inspection signal, based on the quantity and/or orientation of the one or more items within the field of view; and
a processor, coupled to the imager, configured to:
  receive the pass inspection signal or the fail inspection signal;
  advance the movable platform only after receiving a pass inspection signal from the imager; and
  prohibit the movable platform from moving until receipt of another pass signal from the imager based on 1) a further determination of a quantity and/or orientation of one or more items within the field of view; and 2) a comparison of the further determined quantity and/or orientation of the one or more items within the field of view with an expected quantity and/or orientation of the one or more items within the field of view.

19. The system of claim 18, wherein the one or more items includes one or more of a syringe, a syringe needle, or an auto-injector.

20. The system of claim 18, wherein the one or more items comprise one or more first patterns.

21. The system of claim 18, wherein the processor is further configured to:
notify an operator when the movable platform is prohibited from moving.

* * * * *